US012055445B2

United States Patent
Griffin et al.

(10) Patent No.: US 12,055,445 B2
(45) Date of Patent: Aug. 6, 2024

(54) METHOD AND APPARATUS FOR NON-CONTACT TEMPERATURE MEASUREMENT OF A FOOD ITEM

(71) Applicant: Tyson Foods, Inc., Springdale, AR (US)

(72) Inventors: Mark Griffin, Springdale, AR (US); Doug Foreman, Springdale, AR (US); Bill Britting, Rogers, AR (US); Toni Kinsey, Fayetteville, AR (US); Sam Engel, Springdale, AR (US); Jeremy Gerard, Fayetteville, AR (US); Douglas Martin Linn, Cave Springs, AR (US); Travis Scarrow, Fayetteville, AR (US)

(73) Assignee: Tyson Foods, Inc., Springdale, AR (US)

( * ) Notice: Subject to any disclaimer, the term of this patent is extended or adjusted under 35 U.S.C. 154(b) by 318 days.

(21) Appl. No.: 17/689,775

(22) Filed: Mar. 8, 2022

(65) Prior Publication Data

US 2022/0291057 A1 Sep. 15, 2022

Related U.S. Application Data

(60) Provisional application No. 63/158,733, filed on Mar. 9, 2021.

(51) Int. Cl.
   *G01K 13/06* (2006.01)
   *G01B 11/24* (2006.01)
   *G01K 11/00* (2006.01)

(52) U.S. Cl.
   CPC .............. *G01K 13/06* (2013.01); *G01B 11/24* (2013.01); *G01K 11/006* (2013.01)

(58) Field of Classification Search
   CPC ...... G01K 13/06; G01K 11/006; G01B 11/24; G01N 25/20; G01N 33/02; A23L 3/185; A23L 3/361
   See application file for complete search history.

(56) References Cited

U.S. PATENT DOCUMENTS 6,357,911 B1 * 3/2002 Groen ...................... A23L 5/10
   374/E7.042
8,609,168 B2 12/2013 Ceravalls Pujol et al.
(Continued)

FOREIGN PATENT DOCUMENTS

| EP | 3241450 A1 | 11/2017 | |
|---|---|---|---|
| JP | 4437212 B2 * | 3/2010 | ........... A23L 1/0107 |
| WO | 0170087 A2 | 9/2001 | |

OTHER PUBLICATIONS

Hassoun et al. "Monitoring Thermal Treatments Applied to Meat Using Traditional Methods and Spectroscopic Techniques: a Review of Advances over the Last Decade", Food Bioprocess Technol 14, 195-208, Aug. 2020 (Year: 2020).*
(Continued)

*Primary Examiner* — Alexander Satanovsky
*Assistant Examiner* — Asm Fakhruddin
(74) *Attorney, Agent, or Firm* — UB Greensfelder LLP; Mark E. Stallion

(57) ABSTRACT

A method and apparatus for temperature processing a food item. It should be noted that the description provided herein will primarily focus on cooking temperature processing, but cooking is referred to, the process for determining core temperature can also be used for chilling and/or freezing a food item. One implementation of the technology as disclosed and claimed, utilizes a combination of 3D profile scanning camera, mid-range infrared camera, high-resolution encoder-based positioning device, and cook profile settings in order to measure the physical attributes of the
(Continued)

product related to the fully cooked state. The system is measuring at least two aspects that determine the temperature change within an object during the cook process and they are geometry and thermodynamic properties.

16 Claims, 24 Drawing Sheets

(56) References Cited

U.S. PATENT DOCUMENTS

| | | | |
|---|---|---|---|
| 9,414,444 B2 | 8/2016 | Libman et al. | |
| 10,331,102 B2 | 6/2019 | Thrun et al. | |
| 2009/0321428 A1* | 12/2009 | Hyde | H05B 6/6455 |
| | | | 219/702 |
| 2016/0150213 A1 | 5/2016 | Mutti et al. | |
| 2016/0356704 A1 | 12/2016 | Kim et al. | |
| 2017/0224161 A1* | 8/2017 | Li | G05D 23/1917 |
| 2017/0332841 A1 | 11/2017 | Reischmann | |
| 2021/0004550 A9 | 1/2021 | MacIntosh et al. | |

OTHER PUBLICATIONS

Luke N. Belval, "Prediction of Internal Body Temperature using Machine Learning Models"; Master's Thesis. 902; Jul. 2016 (Year: 2016).*

PCT International Search Report and Written Opinion; European Patent Office; Jul. 28, 2022; pp. 1-16.

* cited by examiner

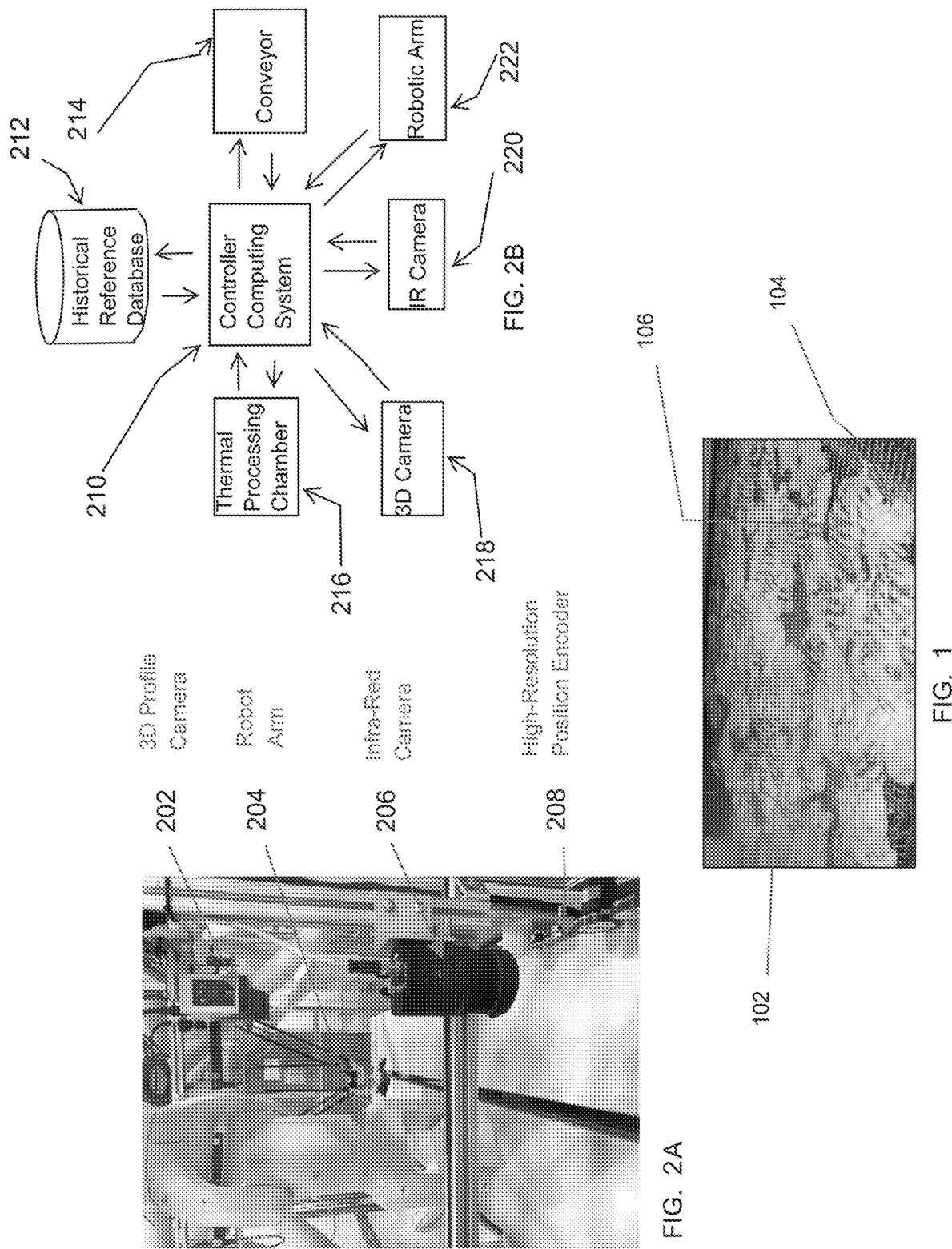

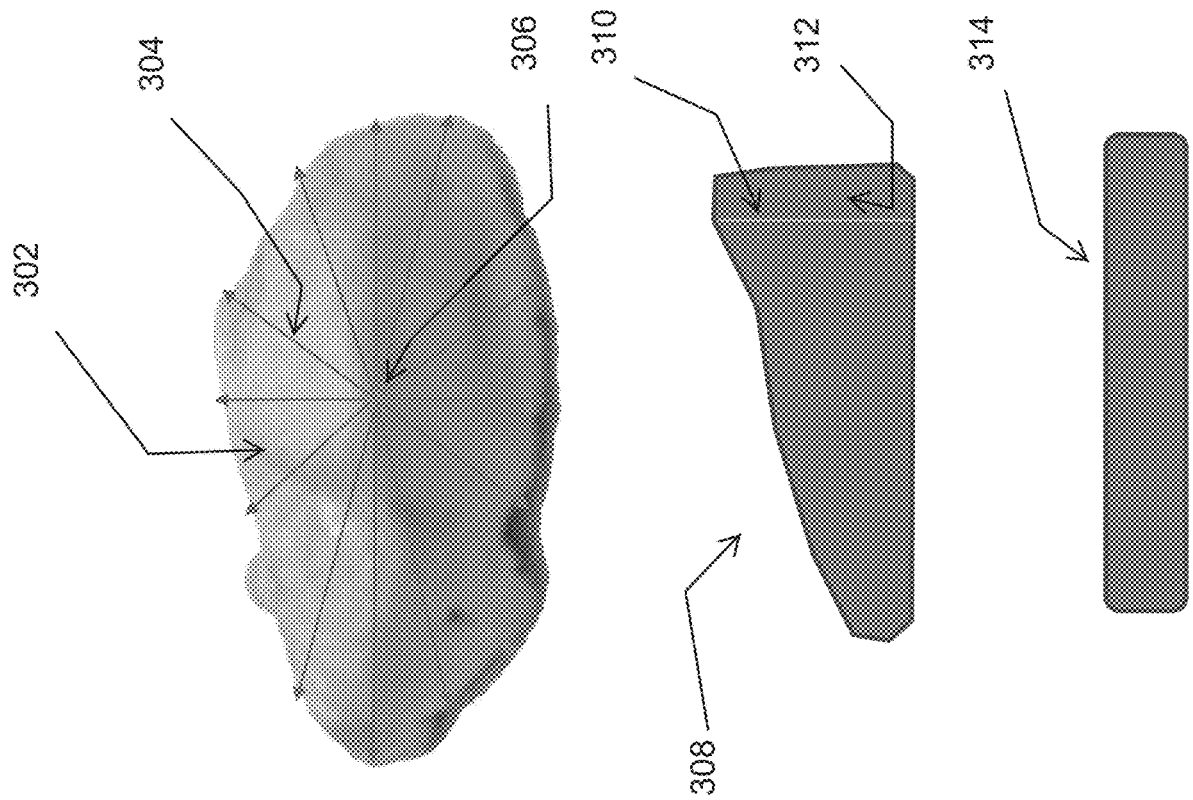

Table 1 Core Temperature Model Data Set

| Core | Height | Humidity | AirSpeed | OvenTemp | CookTime | IRTemp | AirTemp | MODELCore | residual |
|---|---|---|---|---|---|---|---|---|---|
| 161.46 | 110.33 | 36 | 4.8 | 311 | 26.83333 | 152.45 | 74.7 | 162.703071 | 1.545225426 |
| 156.24 | 112.695 | 36 | 4.8 | 311 | 25.56667 | 142.925 | 74.88 | 155.988886 | 0.063058228 |
| 155.16 | 115.16 | 36 | 4.8 | 302.5 | 27.06667 | 145.6 | 74.16 | 157.8911911 | 7.459404805 |
| 149.94 | 115.5891 | 36 | 4.8 | 306.5 | 26.85 | 136.8 | 74.88 | 152.6975904 | 7.604304605 |
| 163.08 | 116.705 | 36 | 4.8 | 311 | 25 | 148 | 73.26 | 157.9327287 | 26.49440161 |
| 179.82 | 117.3366 | 36 | 4.8 | 302.5 | 26.36667 | 179.875 | 74.34 | 175.5498042 | 18.2345722 |
| 153.18 | 119.2 | 36 | 4.8 | 310 | 25.75 | 136.975 | 73.98 | 152.8194406 | 0.130003047 |
| 160.56 | 121.3168 | 36 | 4.8 | 311 | 26.83333 | 155.4625 | 74.7 | 164.0641376 | 12.27898059 |
| 158.58 | 124.1881 | 36 | 4.8 | 311 | 25 | 142.975 | 73.26 | 155.4352843 | 9.889236806 |
| 161.1 | 125.665 | 36 | 4.8 | 310 | 26.98333 | 144.725 | 74.34 | 157.404597 | 13.6560032 |
| 167.22 | 125.89 | 36 | 4.8 | 307.5 | 27.65 | 159.6 | 73.62 | 167.1005702 | 0.014263474 |
| 172.26 | 126.23 | 36 | 4.8 | 328 | 26.23333 | 157.875 | 74.88 | 167.7968187 | 19.9199876 |
| 156.06 | 127.8614 | 36 | 4.8 | 306.5 | 26.28333 | 137.925 | 74.52 | 153.216951 | 8.08292774 |
| 157.86 | 127.93 | 36 | 4.8 | 310 | 25.61667 | 150.4125 | 73.8 | 159.3012883 | 2.07731196 |
| 159.66 | 128.01 | 36 | 4.8 | 311 | 26.83333 | 148.45 | 74.7 | 159.5160844 | 0.0207117 |
| 173.52 | 128.845 | 36 | 4.8 | 311 | 27.3 | 167.225 | 74.7 | 171.5772715 | 3.774193857 |
| 153.36 | 130.445 | 36 | 4.8 | 310 | 25 | 139.775 | 73.26 | 153.78461 | 0.18029363 |
| 157.32 | 130.4851 | 36 | 4.8 | 311 | 26.58333 | 149.7 | 74.88 | 159.9400975 | 6.864911132 |
| 162.9 | 131.36 | 36 | 4.8 | 311 | 26.58333 | 147.2125 | 74.88 | 158.5024356 | 19.33857287 |
| 151.2 | 131.47 | 36 | 4.8 | 306.5 | 26.28333 | 141 | 74.52 | 154.7386755 | 12.52222463 |
| 152.1 | 132.4851 | 36 | 4.8 | 311 | 25.83333 | 136.6125 | 76.5 | 152.6536685 | 0.306548828 |
| 158.76 | 134.715 | 36 | 4.8 | 313.5 | 25 | 145.3 | 73.98 | 156.605695 | 4.64103016 |
| 156.78 | 135.71 | 36 | 4.8 | 313.5 | 26.71667 | 145.3875 | 74.34 | 157.519734 | 0.547206392 |
| 151.38 | 136.14 | 36 | 4.8 | 311 | 26.58333 | 141 | 74.88 | 154.9063853 | 12.43539361 |
| 153 | 137.802 | 36 | 4.8 | 328 | 25 | 141.15 | 73.98 | 157.0199854 | 16.16028294 |
| 158.22 | 138.42 | 36 | 4.8 | 315.5 | 26.2 | 145.2125 | 74.52 | 157.314122 | 0.829614873 |
| 154.98 | 139.44 | 36 | 4.8 | 303 | 25.61667 | 140.025 | 74.34 | 153.5531114 | 2.036011006 |
| 152.28 | 140.9752 | 36 | 4.8 | 313.5 | 25 | 137.65 | 73.98 | 153.1267055 | 0.716910208 |
| 162.9 | 142.0545 | 36 | 4.8 | 315.5 | 26.2 | 161.3 | 74.52 | 165.7246735 | 7.978780432 |
| 171.18 | 142.105 | 36 | 4.8 | 310 | 26.23333 | 188.0875 | 74.16 | 178.5610072 | 54.47926687 |
| 151.02 | 142.4059 | 36 | 4.8 | 313.5 | 26.71667 | 138.25 | 74.34 | 153.2553568 | 4.996819982 |
| 170.28 | 143.825 | 36 | 4.8 | 308 | 27.46667 | 174.85 | 74.88 | 174.4674911 | 17.53508165 |
| 155.88 | 144.455 | 36 | 4.8 | 313.5 | 26.71667 | 155 | 74.34 | 162.4148462 | 42.70421453 |

FIG. 9C

| | | | | | | | |
|---|---|---|---|---|---|---|---|
| 153 | 144.5545 | 36 | 4.8 | 303 | 25.61667 | 142.325 | 74.34 | 154.3823022 | 1.910759462 |
| 161.82 | 144.885 | 36 | 4.8 | 306.5 | 26.28333 | 154.6125 | 74.52 | 160.8609491 | 0.919778604 |
| 169.38 | 145.335 | 36 | 4.8 | 302.5 | 26.36667 | 167.7 | 74.34 | 166.5773034 | 7.855108293 |
| 154.44 | 147.62 | 36 | 4.8 | 310 | 26.23333 | 143.15 | 74.16 | 155.4714404 | 1.063869334 |
| 151.02 | 148.205 | 36 | 4.8 | 302.5 | 25.65 | 139.875 | 74.52 | 153.3537608 | 5.446439244 |
| 157.86 | 169.7871 | 36 | 4.8 | 302 | 28.93333 | 138.825 | 72.56 | 152.8991778 | 24.60975726 |
| 151.56 | 169.88 | 36 | 4.8 | 308 | 25 | 139 | 72.72 | 152.2613133 | 0.491840307 |
| 153.9 | 169.965 | 36 | 4.8 | 305.5 | 25.83333 | 143.925 | 72.54 | 154.3154521 | 0.172600406 |
| 170.1 | 170 | 36 | 4.8 | 309 | 27.51667 | 172.775 | 73.62 | 170.0360365 | 0.004091332 |
| 155.16 | 170.055 | 36 | 4.8 | 312.5 | 26.45 | 148.1625 | 73.62 | 156.6905305 | 2.342523626 |
| 150.84 | 170.2772 | 36 | 4.8 | 309.5 | 25 | 137.05 | 72.54 | 151.7223575 | 0.778554736 |
| 157.5 | 170.815 | 36 | 4.8 | 312 | 26.65 | 143.45 | 73.98 | 154.5224517 | 8.865794031 |
| 155.34 | 171.435 | 36 | 4.8 | 314 | 26.75 | 147.075 | 73.44 | 156.2252388 | 0.783647695 |
| 153.9 | 172.6782 | 36 | 4.8 | 297 | 26.91667 | 143.275 | 73.08 | 155.0071908 | 1.225871558 |
| 174.06 | 172.76 | 36 | 4.8 | 314.5 | 27.58333 | 186.7 | 72.9 | 178.3856135 | 18.71093184 |
| 163.08 | 172.896 | 36 | 4.8 | 314.5 | 25.65 | 158.875 | 73.26 | 160.4605588 | 6.861472247 |
| 165.42 | 172.9604 | 36 | 4.8 | 314.5 | 26.83333 | 158.925 | 72.72 | 161.9646487 | 11.93945289 |
| 154.62 | 173.25 | 36 | 4.8 | 314.5 | 25.65 | 148.0125 | 73.26 | 156.0789072 | 2.128410192 |
| 164.52 | 173.4 | 36 | 4.8 | 312 | 27.41667 | 173.675 | 73.8 | 170.1784874 | 32.01847945 |
| 160.74 | 173.5545 | 36 | 4.8 | 315.5 | 25.95 | 161.0875 | 72.36 | 161.9070303 | 1.361959722 |
| 163.26 | 173.625 | 36 | 4.8 | 314.5 | 26.83333 | 148.4 | 72.72 | 156.7175358 | 42.80383844 |
| 154.98 | 173.66 | 36 | 4.8 | 309.5 | 26.5 | 144.7 | 72.18 | 154.8523195 | 0.01630231 |
| 160.92 | 173.995 | 36 | 4.8 | 317 | 25 | 147.75 | 74.34 | 155.8197573 | 26.0124753 |
| 171 | 174.06 | 36 | 4.8 | 312.5 | 27.2 | 172.975 | 73.62 | 169.305913 | 2.869930735 |
| 167.04 | 174.08 | 36 | 4.8 | 312 | 26.65 | 160.1125 | 73.98 | 161.9454455 | 25.95448577 |
| 163.26 | 174.26 | 36 | 4.8 | 315.5 | 26.85 | 160.85 | 72.54 | 162.8866442 | 0.139394581 |
| 151.2 | 174.92 | 36 | 4.8 | 317 | 25 | 145 | 74.34 | 154.765605 | 12.71353867 |
| 154.26 | 176.025 | 36 | 4.8 | 308 | 25.76667 | 139 | 73.08 | 152.2662171 | 3.975170085 |
| 159.66 | 177.24 | 36 | 4.8 | 314 | 26.75 | 151.8875 | 73.44 | 158.0065545 | 2.733551436 |
| 151.2 | 177.385 | 36 | 4.8 | 309.5 | 27.21667 | 139 | 72.36 | 152.0861123 | 0.785195 |
| 156.96 | 177.48 | 36 | 4.8 | 315.5 | 26.66667 | 151.0375 | 72.36 | 157.2171184 | 0.066109856 |
| 157.5 | 178.09 | 36 | 4.8 | 311.5 | 26.66667 | 153.975 | 73.62 | 158.7015331 | 1.443681713 |
| 167.04 | 178.19 | 36 | 4.8 | 312.5 | 26.45 | 161.4375 | 73.62 | 161.8289039 | 27.15552248 |
| 156.96 | 178.27 | 36 | 4.8 | 317 | 26.08333 | 150.675 | 74.34 | 157.1939416 | 0.05472866 |

FIG. 9D

| | | | | | | | |
|---|---|---|---|---|---|---|---|
| 165.6 | 178.44 | 36 | 4.8 | 308 | 27.2 | 168.5875 | 73.08 | 165.9335631 | 0.111264314 |
| 155.16 | 178.835 | 36 | 4.8 | 307.5 | 25 | 145 | 73.08 | 153.5346696 | 2.64169886 |
| 159.12 | 179.7624 | 36 | 4.8 | 317 | 25.7 | 167.5 | 73.8 | 163.6629823 | 20.63868808 |
| 157.5 | 180.165 | 36 | 4.8 | 317 | 25.36667 | 147.6875 | 73.26 | 155.4742191 | 4.103788173 |
| 150.48 | 180.9 | 36 | 4.8 | 314.5 | 25 | 136.425 | 72.9 | 151.2950576 | 0.664318836 |
| 151.74 | 180.9653 | 36 | 4.8 | 309.5 | 27.21667 | 146.475 | 72.36 | 155.3312717 | 12.89723262 |
| 152.64 | 180.9703 | 36 | 4.8 | 317 | 25.36667 | 146.7375 | 73.26 | 155.0533055 | 5.824043642 |
| 152.1 | 181.315 | 36 | 4.8 | 317 | 25.7 | 142.15 | 73.8 | 153.3375437 | 1.531514446 |
| 172.26 | 181.6782 | 36 | 4.8 | 314.5 | 27.58333 | 180.3875 | 72.9 | 173.1836158 | 0.853066106 |
| 152.64 | 181.6832 | 36 | 4.8 | 307.5 | 25 | 148.025 | 72.72 | 154.1889008 | 2.399093648 |
| 158.04 | 182.21 | 36 | 4.8 | 317 | 25.68333 | 154.4375 | 74.16 | 158.0724824 | 0.031055108 |
| 152.82 | 182.4554 | 36 | 4.8 | 315.5 | 25 | 147.5 | 72.36 | 154.8388925 | 4.075926846 |
| 149.94 | 182.61 | 36 | 4.8 | 309.5 | 25 | 134.45 | 72.54 | 150.4631165 | 0.273650889 |
| 165.6 | 183.405 | 36 | 4.8 | 317 | 25.7 | 160.75 | 73.8 | 160.4476994 | 26.54620148 |
| 163.62 | 184.12 | 36 | 4.8 | 309 | 25.85 | 161.3 | 73.8 | 159.6275597 | 15.93957951 |
| 150.3 | 184.3515 | 36 | 4.8 | 297 | 25 | 141.625 | 72.9 | 151.8712333 | 2.458774156 |
| 158.4 | 185.96 | 36 | 4.8 | 314 | 25.96667 | 152.625 | 73.26 | 156.8970087 | 2.25898274 |
| 165.24 | 186.005 | 36 | 4.8 | 309.5 | 28.65 | 170.9375 | 72.72 | 168.916831 | 13.519086 |
| 161.46 | 186.896 | 36 | 4.8 | 317 | 25.68333 | 170.575 | 74.16 | 163.7978729 | 5.455649529 |
| 155.16 | 187.17 | 36 | 4.8 | 314 | 25 | 152.275 | 73.26 | 155.723859 | 0.317936918 |
| 158.4 | 187.599 | 36 | 4.8 | 308 | 25.76667 | 150.7625 | 73.08 | 155.4474251 | 8.717698737 |
| 165.6 | 188.315 | 36 | 4.8 | 309 | 27.51667 | 172.85 | 73.62 | 167.2936665 | 2.86850623 |
| 170.64 | 190.025 | 36 | 4.8 | 309.5 | 28.65 | 179.6125 | 72.72 | 173.2241548 | 6.677856169 |
| 153.54 | 190.5347 | 36 | 4.8 | 312.5 | 25 | 140.8 | 73.44 | 151.916692 | 2.635128994 |
| 151.92 | 190.605 | 36 | 4.8 | 317 | 25.36667 | 161.175 | 73.26 | 159.1968363 | 52.95234709 |
| 154.8 | 193.525 | 36 | 4.8 | 307.5 | 26.6 | 145.0375 | 73.08 | 153.5702424 | 1.512303755 |
| 151.2 | 195.1782 | 36 | 4.8 | 317 | 25 | 144.425 | 74.34 | 152.9175523 | 2.949986012 |
| 150.3 | 195.6584 | 36 | 4.8 | 317 | 26.08333 | 153.05 | 74.34 | 156.3043122 | 36.05176498 |
| 166.68 | 195.98 | 36 | 4.8 | 305.5 | 26.6 | 170 | 72.54 | 162.3762343 | 18.52239947 |
| 174.96 | 196.055 | 36 | 4.8 | 312.5 | 27.2 | 182.475 | 73.62 | 170.1476516 | 23.15869732 |
| 149.94 | 197.797 | 36 | 4.8 | 307.5 | 25 | 143 | 73.08 | 151.7147563 | 3.149759924 |
| 151.38 | 198.0792 | 36 | 4.8 | 314 | 25 | 144.2 | 73.26 | 152.3631059 | 0.96649723 |
| 152.46 | 198.5594 | 36 | 4.8 | 309.5 | 27.93333 | 150.35 | 72.72 | 155.6721994 | 10.31822524 |
| 158.76 | 199.205 | 36 | 4.8 | 308 | 25.76667 | 159 | 73.08 | 156.7964203 | 3.855645194 |

FIG. 9E

| | | | | | | |
|---|---|---|---|---|---|---|
| 148.86 | 199.53 | 36 | 4.8 | 307.5 | 25 | | 73.08 | 152.0396519 | 10.11018508 |
| 176.22 | 200.703 | 36 | 4.8 | 314.5 | 27.2 | 177.125 | 73.44 | 167.0980182 | 83.21055199 |
| 158.04 | 201.104 | 36 | 4.8 | 312 | 26.61667 | 161.2125 | 74.34 | 158.9456253 | 0.820157196 |
| 152.28 | 201.1931 | 36 | 4.8 | 314.5 | 25 | 139.275 | 72.36 | 150.8125692 | 2.153353125 |
| 153.54 | 202.4604 | 36 | 4.8 | 312 | 25 | 143.2375 | 73.98 | 151.6136183 | 3.710946348 |
| 166.86 | 203.045 | 36 | 4.8 | 308 | 27.2 | 178.5875 | 73.08 | 166.4224486 | 0.191451268 |
| 150.12 | 203.07 | 36 | 4.8 | 312 | 25 | 144.875 | 73.44 | 151.9647498 | 3.403101643 |
| 165.42 | 205.3564 | 36 | 4.8 | 309.5 | 28.65 | 180.375 | 72.72 | 170.7001549 | 27.8800354 |
| 149.94 | 206.055 | 36 | 4.8 | 314.5 | 25 | 143.125 | 72.36 | 151.3994428 | 2.129973144 |
| 151.56 | 206.38 | 36 | 4.8 | 312 | 25 | 149.025 | 73.98 | 152.6540152 | 1.196869276 |
| 161.28 | 207.405 | 36 | 4.8 | 314.5 | 25.65 | 161.6 | 73.26 | 157.0421367 | 17.95948557 |
| 152.28 | 209.07 | 36 | 4.8 | 314.5 | 26.36667 | 152.0375 | 73.44 | 154.3500288 | 4.285019053 |
| 154.08 | 210.89 | 36 | 4.8 | 312.5 | 25 | 143.425 | 73.44 | 150.929038 | 9.928561669 |
| 198.9 | 159.005 | 36 | 4.8 | 312 | 34.08333 | 187.2 | 73 | 195.4926552 | 11.60999838 |
| 150.3 | 160.8209 | 36 | 4.8 | 312 | 25 | 135.375 | 73 | 151.6195639 | 1.741248819 |
| 187.56 | 161.415 | 36 | 4.8 | 307 | 32.96667 | 179.8375 | 73 | 186.7258204 | 0.69585557 |
| 153.72 | 164.355 | 31 | 4.8 | 303.5 | 27.6 | 141.025 | 73 | 154.2373157 | 0.267615538 |
| 163.62 | 169.4726 | 36 | 4.8 | 312 | 25 | 145.7 | 73 | 154.79945 | 77.80210176 |
| 159.84 | 169.6816 | 36 | 4.8 | 303 | 30.28333 | 146.775 | 73 | 157.3740522 | 6.08089841 |
| 203.58 | 169.99 | 36 | 4.8 | 307 | 32.96667 | 188.725 | 73 | 193.6506425 | 98.59213964 |
| 152.64 | 170.7122 | 29 | 4.8 | 299 | 27.78333 | 136 | 73 | 152.1544272 | 0.235780957 |
| 154.62 | 174.9751 | 36 | 4.8 | 303 | 25 | 142.7 | 73 | 152.7941048 | 3.333893397 |
| 189.72 | 175.2921 | 36 | 4.8 | 307 | 32.96667 | 183.925 | 73 | 188.0394273 | 2.824324661 |
| 165.06 | 176.6386 | 36 | 4.8 | 312 | 25 | 149.2 | 73 | 155.4380356 | 92.58219889 |
| 156.6 | 176.791 | 29 | 4.8 | 303.5 | 32.68333 | 166.475 | 73 | 172.3702765 | 248.7016218 |
| 153.54 | 179.1443 | 31 | 4.8 | 303.5 | 27.6 | 153.95 | 73 | 159.4511397 | 34.94157198 |
| 148.32 | 179.1493 | 29 | 4.8 | 299 | 33.2 | 137.85 | 73 | 148.6161214 | 0.087687893 |
| 174.24 | 181.1244 | 36 | 4.8 | 312 | 31.58333 | 176.875 | 73 | 178.0801627 | 14.74684931 |
| 160.56 | 181.1535 | 29 | 4.8 | 299 | 27.78333 | 143.475 | 73 | 155.0555596 | 30.2988642 |
| 155.16 | 181.7114 | 29 | 4.8 | 303.5 | 25 | 139.175 | 73 | 151.6056164 | 12.63364291 |
| 154.8 | 182.5792 | 31 | 4.8 | 303.5 | 27.6 | 145.3125 | 73 | 155.2093367 | 0.162357999 |
| 158.22 | 182.8856 | 29 | 4.8 | 307 | 30.28333 | 155.325 | 73 | 161.1974951 | 8.865476813 |
| 164.52 | 182.9502 | 30 | 4.8 | 303.5 | 30.11667 | 152.5875 | 73 | 159.9940873 | 20.48388575 |
| 147.6 | 187.215 | 29 | 4.8 | 303.5 | 25 | 140.9 | 73 | 151.7505743 | 17.22726668 |

FIG. 9F

| | | | | | | |
|---|---|---|---|---|---|---|
| 154.26 | 187.53 | 29 | 4.8 | 299 | 30.46667 | 140.3 | 73 | 152.8402206 | 2.015773636 |
| 172.62 | 187.785 | 36 | 4.8 | 312 | 34.08333 | 167.025 | 73 | 168.7150361 | 15.24874326 |
| 147.42 | 188.2475 | 29 | 4.8 | 307 | 25 | 133.375 | 73 | 149.9392231 | 6.346485034 |
| 152.64 | 188.2488 | 29 | 4.8 | 307 | 27.65 | 135.725 | 73 | 150.0525406 | 6.694946392 |
| 146.16 | 189.65 | 36 | 4.8 | 303 | 25 | 136 | 73 | 150.5159227 | 18.97406295 |
| 152.82 | 191.078 | 31 | 4.8 | 303.5 | 27.6 | 143 | 73 | 153.5697746 | 0.562161983 |
| 146.34 | 191.9104 | 36 | 4.8 | 303 | 25 | 136 | 73 | 150.4198053 | 16.64481117 |
| 154.8 | 191.955 | 36 | 4.8 | 312 | 31.58333 | 150.6 | 73 | 154.9312518 | 0.017227027 |
| 151.56 | 192.8955 | 29 | 4.8 | 299 | 25 | 134.025 | 73 | 150.0682693 | 2.225260615 |
| 158.04 | 192.9204 | 36 | 4.8 | 312 | 34.08333 | 165.3875 | 73 | 166.17707 | 66.21190887 |
| 157.5 | 193.0396 | 36 | 4.8 | 312 | 31.58333 | 151.4625 | 73 | 155.4803551 | 4.078965474 |
| 148.5 | 194.085 | 29 | 4.8 | 303.5 | 32.68333 | 136.7375 | 73 | 145.310959 | 10.16998238 |
| 149.04 | 194.6318 | 36 | 4.8 | 303 | 30.28333 | 140.925 | 73 | 151.5780957 | 6.441930016 |
| 153.9 | 195.34 | 36 | 4.8 | 303 | 32.96667 | 147.225 | 73 | 153.6354619 | 0.069980404 |
| 152.82 | 197.13 | 36 | 4.8 | 303 | 30.28333 | 139.25 | 73 | 150.3442118 | 6.129527265 |
| 150.48 | 199.2772 | 29 | 4.8 | 303.5 | 25 | 146.3375 | 73 | 152.1428891 | 2.765200029 |
| 151.2 | 200.0149 | 30 | 4.8 | 303.5 | 30.11667 | 143.0375 | 73 | 152.3722821 | 1.374245381 |
| 162.9 | 200.4878 | 36 | 4.8 | 312 | 28.86667 | 156.6375 | 73 | 158.755363 | 17.17801609 |
| 152.1 | 200.9353 | 29 | 4.8 | 307 | 27.65 | 137 | 73 | 149.8104538 | 5.242021992 |
| 147.96 | 201.2878 | 29 | 4.8 | 303.5 | 25 | 136 | 73 | 149.9655868 | 4.022378436 |
| 169.02 | 201.5224 | 29 | 4.8 | 307 | 30.28333 | 169.5 | 73 | 168.0070934 | 1.025979878 | mean
158.7104

TSR
1952.926967

FIG. 9G

Position data passed to robot controller for exact positioning to identified location with fast-response temperature probe.

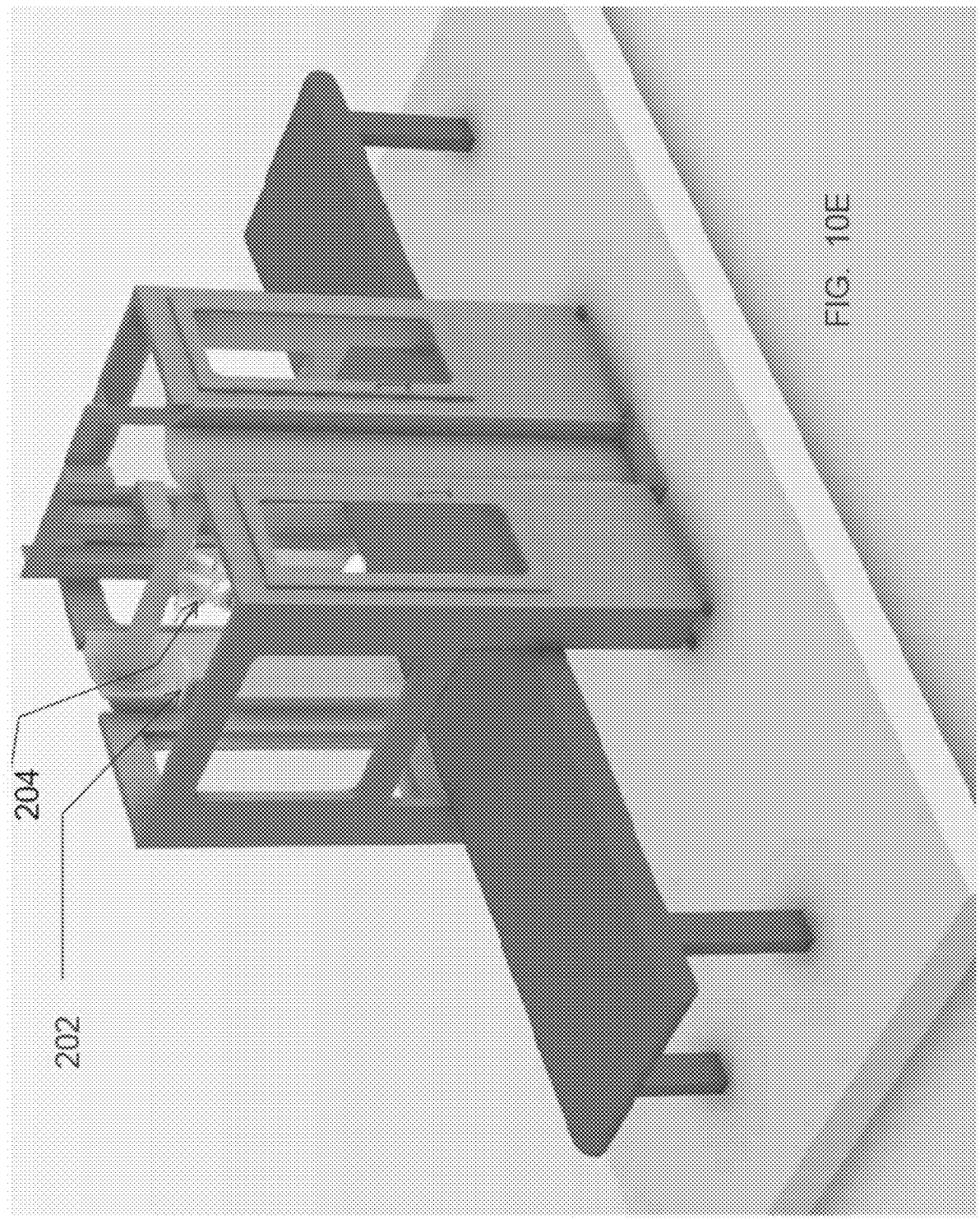

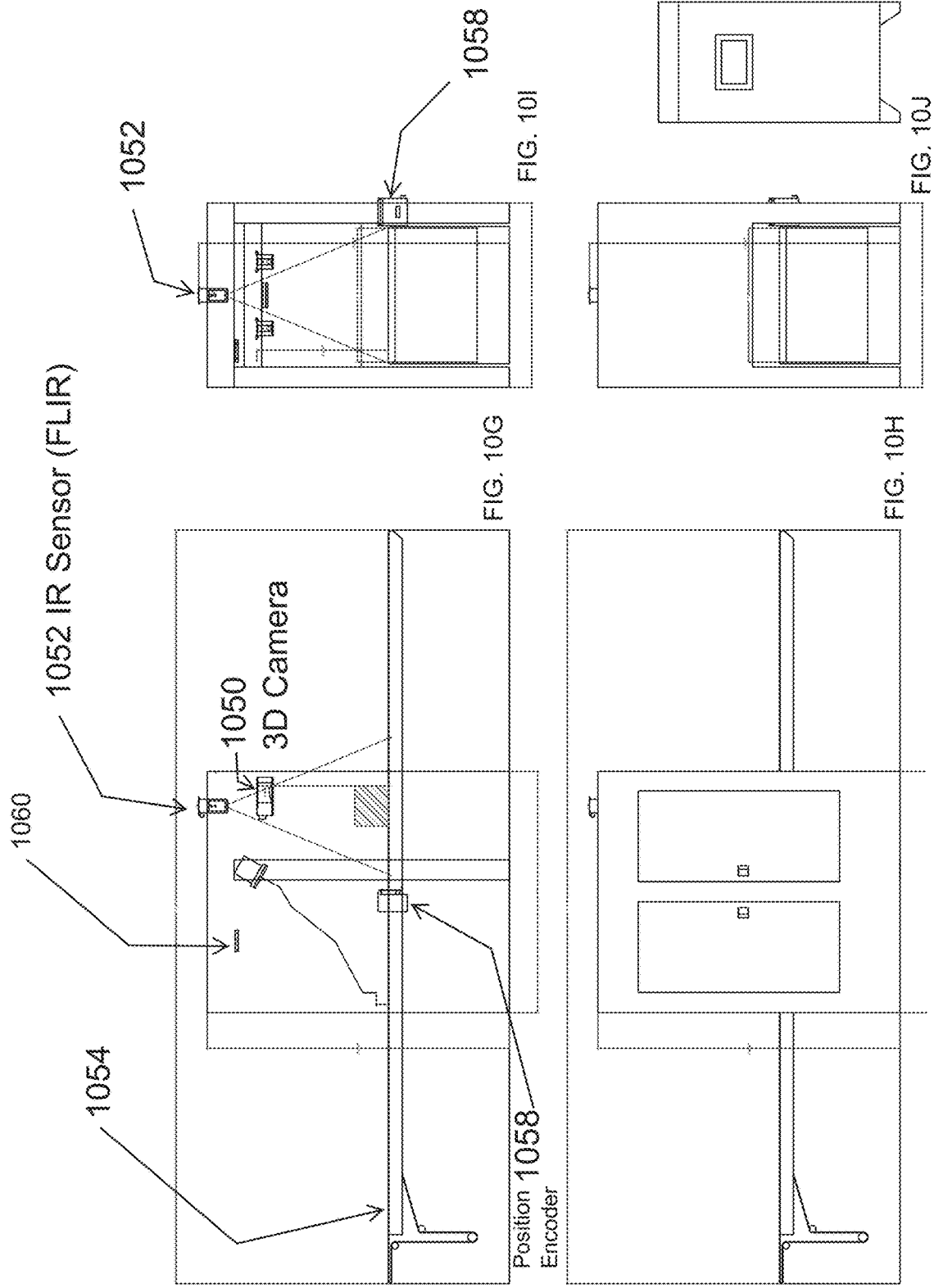

Selection of Temperature Probing Point within Multiple Piece Flow

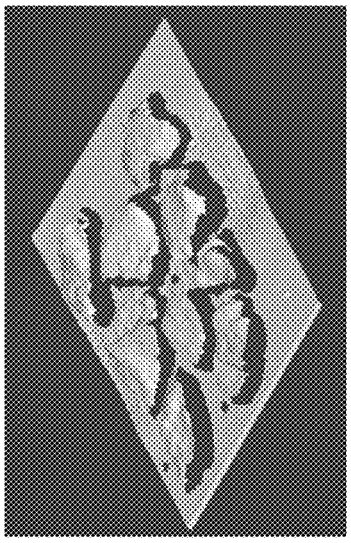

Upon activation, an image is triggered from the 3D displacement camera. The image has been adjusted for the belt surface height and calibrated with the robot coordinates system. A 3D surface image is produced.

FIG. 12A

This is an overhead vision camera shot of the same area of belt to convey how the image is processed.

FIG. 12B

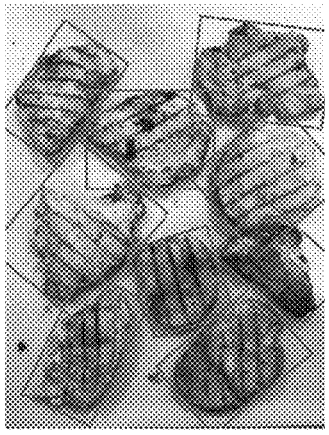

All structures that are above the conveyor by a certain minimum height and conform to a minimum size are identified as objects. In this case, there are 9 objects within the 3D camera frame.

FIG. 12C

Selection of Temperature Probing Point within Multiple Piece Flow

Each object is further processed according to the maximum height of the object and its parameter to identify the mound. The mound is considered a contiguous high area not adjoining the outer parameter by half of the maximum height value.

The average height of the center of this mound is identified for the object. The object with the highest value is selected.

FIG. 12D

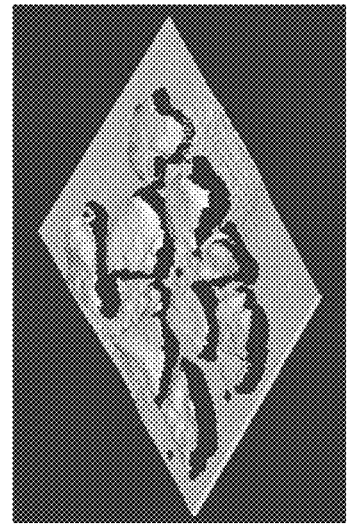

From the selected object, the center of the mound area is identified as the core location to be used as coordinates for the temperature probe measurement. In this case, the 3rd piece from the left of the back row is selected by the criterion. The point for the temperature probe to be positioned at is highlighted in light green. The 3-dimensional coordinates for this point is passed to the robot controller after processing of the image.

FIG. 12E

METHOD AND APPARATUS FOR NON-CONTACT TEMPERATURE MEASUREMENT OF A FOOD ITEM

CROSS REFERENCE

This application claims priority to and the benefit of U.S. Provisional Patent Application No. 63/158,733, entitled Method and Apparatus for Non-Contact Temperature Measurement of a Food Item, filed Mar. 9, 2021 whereby the contents of which are incorporated herein by reference in their entirety.

BACKGROUND

Field

This technology as disclosed herein relates generally to processing a food item and, more particularly, to temperature testing a food item.

Background of Art

There are various types of temperature or thermal food processing methods and devices for heating, cooking, chilling and/or freezing a food item and many of these devices are controlled by user's selection of parameters such as time and temperature. Automatic selection of these heating, cooking, chilling and/or freezing parameters are convenient to the user and could also improve the cooking results by eliminating human error. However, in order to control a temperature process accurately, it is necessary to know the key properties of the food during the temperature processing whether heating, cooking, partially cooking, chilling and/or freezing. One key property of the food item being processed that should be known is the core temperature, which changes as the food is temperature processed such as when a food item is cooked. The core temperature of the food is an important measurement of cooking doneness. For a certain type of food, it should be higher than a certain value to kill the harmful bacteria that cause foodborne illness but should not be too high in order to avoid overcooking. As a result, to ensure safety, foods are suggested to be cooked for an appropriate period of time and with a suitable internal temperature (range). Similarly, for food safety reasons, if a food item is to be frozen for preserving the integrity of the food item to increase the shelf life, then it is important that the food item reaches a temperature that actually results in freezing the item.

To determine if an item of food is cooked based on the core temperature, or sufficiently chilled or frozen, invasive methods are possible, but these can cause damage to the food when detecting core temperature, particularly when inserting a probe in a food item and these methods are often performed manually, which can be very labor intensive, and can have significant inconsistencies between operators who subjectively determine where to invasively probe a food item in order to determine its core temperature. Non-invasive methods such as infrared sensing have limited penetration ability so are usually used to detect the surface temperature, but by itself does not determine the core temperature of the food item. Also, depending on the size of the food item and the volume of the food item and the speed at which the food item is being processed, an operator physically probing a food item cannot practically physically probe each and every individual food item, therefore, only a sampling of the food items is probed such that inaccuracies can occur given that all of the food items being processed will not have the same volume. By way of illustration, product's internal temperature is an important control point in the process for fully cooking a food item, with the criterion being to demonstrate that the coldest point in the product has reached an "instantaneous" microbiological kill point of 160° F.

Temperature probing performed manually typically occurs at the end of each fully cooked process by a "temptaker". For example, this person measures the internal temperature of 10 individual pieces or items (for example— chicken breast) and records them within a computer based system as a statistical sample. In some cases the temp-taker uses a hand-held thermometer probe that is inserted into an area of the product item that the temp-taker operator thinks is the thickest section of a randomly selected piece or item. This is a very visually subjective operation. By way of illustration, this procedure is repeated approximately every 10 to 15 minutes throughout the production shift. What is physically measured is as much as 60 pieces per hour out of a production of 35,000 (0.17%) to 90,000 (0.07%) pieces per hour on a typical cook line. These methods can have significant inconsistencies.

There is therefore a need for a more comprehensive and a non-invasive way to detect the core temperature of an item being cooked or otherwise temperature processed. A better apparatus and/or method is needed for improving the monitoring the core temperature of a food item being processed to determine if the food item is sufficiently cooked and/or frozen.

SUMMARY

The technology as disclosed herein includes a method and apparatus for temperature processing a food item. It should be noted that the description provided herein will primarily focus on cooking temperature processing, however, although cooking is referred to, the process for determining core temperature can also be used for chilling and/or freezing a food item. One implementation of the technology as disclosed and claimed, utilizes a combination of a 3D profile scanning camera, mid-range infrared camera, high-resolution encoder-based positioning device, and cook profile settings in order to measure the physical attributes of the product related to the fully cooked state. The system is measuring at least two aspects that determine the temperature change within an object during the cook process and they are geometry and thermodynamic properties.

The objective of the technology as disclosed and claimed herein is to provide a non-contact temperature measuring system that is disposed to receive a food item as it completes a thermal temperature process, by way of illustration, at the exit end of a full cook process, as a food item exits a linear oven on a conveyor traversing from an interior cooking chamber of the oven and exits so that the food item can be examined to determine the coldest temperatures of items flowing in the product stream, where the coldest temperature measurement is to be used against an alarm level (a temperature level or range, below which is not acceptable resulting in an alert) to monitor and maintain food safety using the speed and reliability of technology. The scope of the technology as disclosed is focused towards a methodology for faster, more reliable, and a more representative measure of the internal temperature of a cooked product at its core, which is a point within the food item that is the furthest distance from any side, making objective measures instead of subjective measure and measuring a significant portion of the product, and may be even all.

One implementation of the technology as disclosed includes a controller that controls an oven to perform a time and temperature cooking profile that cooks the one or more items at one or more temperatures for a duration of time for each of the one or more temperatures. By way of illustration, in the case of a linear oven where the food items are conveyed on a conveyor that through the cooking chamber of the linear oven, the food item is conveyed on the conveyor at a speed to achieve the appropriate dwell time in the cooking chamber based on the temperature profile of the cooking chamber. The controller accesses stored temperature and time parameters and profiles for standard cooking profiles for various types of food items. By way of illustration, the time and temperature profile may vary between a boneless chicken breasts, a bone-in chicken breast and a ground beef patty. The controller will control the conveyor speed to determine the dwell time in the cooking chamber and the controller also controls the temperature profile of the cooing chamber.

One implementation of the technology utilizes a 3D profile scanning camera disposed to scan a food item when it exits or completes the time and temperature profile to determine the geometry of the food. In the case of the linear oven, the 3D profile scanning camera is disposed adjacent the exit end of the cooking chamber and scans the food item as it is conveyed out the exit end of the cooking chamber. The controller controls the scanner to scan a 3D image of the food item and transmit the scan data representative of the 3D image to the controller, which electronically stores the data in a memory. The three dimensional geometric surface and volume are calculated for the food item from the 3D scan data. The core position of the food item is calculated based on the calculated three dimensional surface and volume. The controller utilizes data being transmitted from position encoder monitor and determine the position of the food item as it is being conveyed and thereby monitors and determines the position of the core of the food item and thereby controls a robotic arm to insert a temperature probe at the core position to measure the temperature of the food item at the core position. An encoder is a sensor which turns a position into an electronic signal. There are two forms: Absolute encoders give an absolute position value. Incremental encoders count movement rather than position. With detection of a datum position and the use of a counter, an absolute position may be derived. The controller utilizes data being transmitted from position encoder monitor and determine the position of the food item as it is being conveyed and thereby monitors and determines the position of the core of the food item and thereby controls an Infra-RED scanner to scan the food item and generate infra-red scan data representative of an infra-red heat map of the exterior of the food item. The temperature probe transmits the temperature at the core position to the controller and the infra-red scanner transmits the heat map, both of which are correlated to the temperature measured by the temperature probe, the geometry as determined by the 3D camera, type of food item and the time/temperature profile exposure for the food item and controller electronically stores the data in a correlated format for future reference thereby building a reference database. For each record in the database, the heat map from the infrared sensor and correlating measured core temperature includes a correlated geometry, food type and time/temperature profile.

A learning function continuously monitors the reference database correlating the heat map to the actual probed temperature and to the time/temperature profile. The learning function continuously learns the relationship between the heat map and the actual measured core temperature when considering the type of food item, the geometry/volume and the time and temperature profile. As the learning function continues to learn, the learning function may periodically adjust the time and temperature profile for a given type of food item based on the learning function determining that either the appropriate core temperature is not regularly being met, and/or, the target core temperature is being exceeded thereby over cooking the food item. The learning function updates the reference database as needed by adjusting the time/temperature profile to consistently achieve the targeted core temperature for a given food item.

For one implementation of the technology as disclosed and claimed, once the learning function and the reference database has reach a statistically sufficient sized data set for a type of food item and a type of varying geometries such that the core temperature can be predicted without physically probing the food item, the regularity of the physical insertion of the probe can be ceased completely or significantly lessened and monitored periodically only to make sure the accuracy of the predictive capability is maintained including being able to flag whether the oven itself is not outputting the heat transfer function as per normal. Further, it should be reiterated that this technology as disclosed and claimed applies to any temperature processing including, warming, smoking, partially cooking, fully cooking, chilling and/or freezing an item.

The features, functions, and advantages that have been discussed can be achieved independently in various implementations or may be combined in yet other implementations further details of which can be seen with reference to the following description and drawings. These and other advantageous features of the present technology as disclosed will be in part apparent and in part pointed out herein below.

BRIEF DESCRIPTION OF THE DRAWING

For a better understanding of the present technology as disclosed, reference may be made to the accompanying drawings in which:

FIG. 1 is an illustration of food items transitioning from temperature processing;

FIGS. 2A and 2B is an illustration of a 3D Profile Camera, Robot Arm, Infrared Camera and position encoder positioned to capture the food item as it completes temperature processing;

FIGS. 3A, 3B and 3C, is an illustration of how a core position of a food item is determined;

FIG. 9C through FIG. 9H is an illustration of a core temperature model data set;

FIGS. 10E through 10J are an illustration of the non-contact system.

FIGS. 12A through 12E, are an illustration of the selection of a temperature probing point within a multiple piece food item flow.

Figure 4:
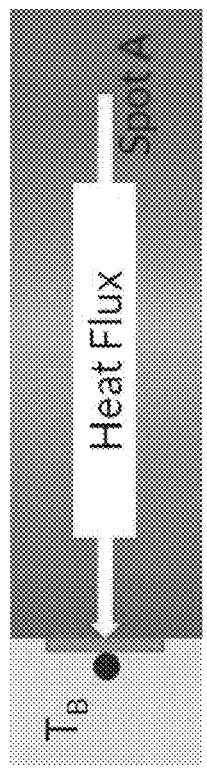
FIG. 4 is an illustration, of a heat flux profile.

While the technology as disclosed is susceptible to various modifications and alternative forms, specific implementations thereof are shown by way of example in the drawings and will herein be described in detail. It should be understood, however, that the drawings and detailed description presented herein are not intended to limit the disclosure to the particular implementations as disclosed, but on the contrary, the intention is to cover all modifications, equivalents, and alternatives falling within the scope of the present technology as disclosed and as defined by the appended claims.

DESCRIPTION

According to the implementation(s) of the present technology as disclosed, various views are illustrated in FIGS. 1-12 and like reference numerals are being used consistently throughout to refer to like and corresponding parts of the technology for all of the various views and figures of the drawing. Also, please note that the first digit(s) of the reference number for a given item or part of the technology should correspond to the FIG. number in which the item or part is first identified. Reference in the specification to "one embodiment" or "an embodiment"; "one implementation" or "an implementation" means that a particular feature, structure, or characteristic described in connection with the embodiment or implementation is included in at least one embodiment or implementation of the invention. The appearances of the phrase "in one embodiment" or "in one implementation" in various places in the specification are not necessarily all referring to the same embodiment or the same implementation, nor are separate or alternative embodiments or implementations mutually exclusive of other embodiments or implementations.

The technology as disclosed herein includes a method and apparatus for temperature processing a food item. It should be noted that the description provided herein will primarily focus on cooking temperature processing, however, although cooking is referred to, the process for determining core temperature can also be used for chilling and/or freezing a food item. One implementation of the technology as disclosed and claimed, utilizes a combination of 3D profile scanning camera, mid-range infrared camera, high-resolution encoder-based positioning device, and cook profile settings in order to measure the physical attributes of the product related to the fully cooked state. The system is measuring at least two aspects that determine the temperature change within an object during the cook process and they are geometry and thermodynamic properties.

One implementation of the present technology as disclosed comprising a combination of a 3D profile scanner, a positioning encoder, an infrared scanner and robotically controlled temperature probe teaches a novel apparatus and method for automatically determining the core temperature of a food item being temperature processed.

The details of the technology as disclosed and various implementations can be better understood by referring to the figures of the drawing. Referring to FIGS. 1 and 2 illustrations are provided of system at the exit 102 of a full cook process to determine the coldest temperatures in the product stream to be used against an alarm level to monitor and maintain food safety using the speed and reliability of technology. The technology as disclosed and claimed provides a methodology for faster, more reliable, and more representative measure of the internal temperature of the cooked product 106. The technology makes objective measures using a robotic arm 204 to control a physical temperature probe and/or using learning function instead of subjective measure. The technology as disclosed and claimed allows for the measure a more significant portion of the product, and may be even all. The objective measure of temperature using a temperature probe being inserted by the robotic arm, can be correlated with non-contact temperature measurements of the same item to calibrate, adjust or check the accuracy of the non-contact temperature measurement method. The objective measure can be utilized during production as needed for accuracy checks or during the learning mode of a newly installed system. Once a system install has matured, one implementation of the mature install or like installs may have the temperature probe and robotic arm substantially eliminated. The technology as disclosed and claimed utilizes a combination of 3D profile scanning camera 202, mid-range infrared camera 206, an encoder-based positioning device 208 to locate the position of the product being conveyed on the conveyor 104 and cook profile settings to measure the physical attributes of the product related to the fully cooked state. The technology as disclosed is measuring two aspects that determine the temperature change within an object during the cook process, which includes geometry and thermodynamic properties.

Referring to FIGS. 3A, 3B and 3C, an illustration of how a core position 306 of a food item 302 is determined is shown, which is the furthest distance 304 from all surfaces. The Core location or core position 306 is defined as the position within the object that is farthest from all surfaces. This can be determined when the item is scanned with a 3D Profile Scanner and the outer surface geometry is thereby determined. Functionally, this represents the location that requires the longest overall path for the transmission of heat energy from the outer surface. For a contoured object having a contoured outer surface geometry (such as the chicken breast fillet in FIG. 3A), this is not necessarily the center of the thickest section. The core position cannot be simplistically determined by identifying the thickest portion of the item, which is simplistically displayed in FIG. 3B, the thickest section located near an edge (a distance 312) would give an erroneous position for the core location. Likewise, a uniform shaped object 314 such as FIG. 3C has no thickest height, therefore identifying the thickest area is not the appropriate method, however, when a food item is probed manually for temperature, the "Temp-Taker" may be visually persuaded to probe the thickest area as there is little likelihood that an operator can visually determine the core position.

Figure 5:
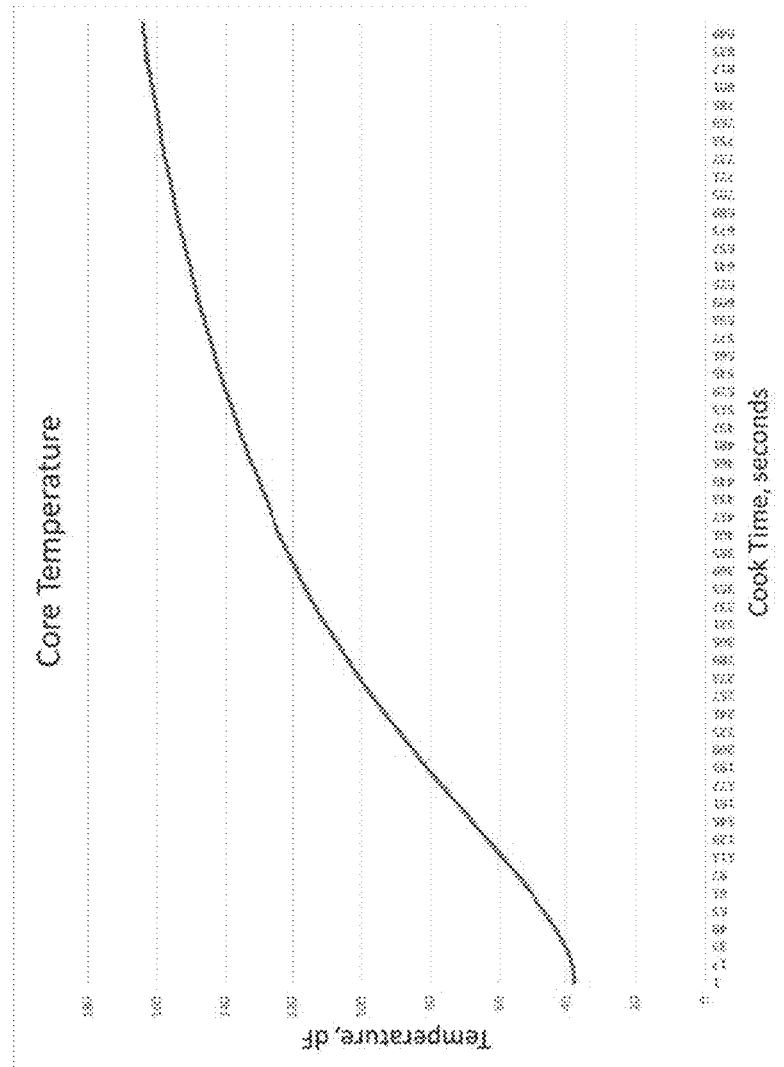
FIG. 5 is an illustration of a core temperature profile.

The Heat Transfer of an item of concern is important. All materials, including food items by way of illustration, have properties that control the rate of heat transfer, the amount of heat transfer, and the resulting change in temperature. These properties are: thermal conductivity, intermolecular phase alignment, specific heat, and mass transfer. The gradient of temperature, or heat flux as illustrated in FIG. 4, through the material is fairly large in the case of hot, fast cook operations used in chicken processing. In the case of a chicken muscle, by way of illustration, a large portion of the mass is water. Therefore, the heat transfer in chicken is largely governed by the thermal properties of water. FIG. 5 shows the thermal graph of a chicken breast cook process, which illustrated the temperature change over the cook time. If an object is constructed of disparate materials, such as fat and lean, the properties of each change the overall performance of heat transfers.

Figure 6:
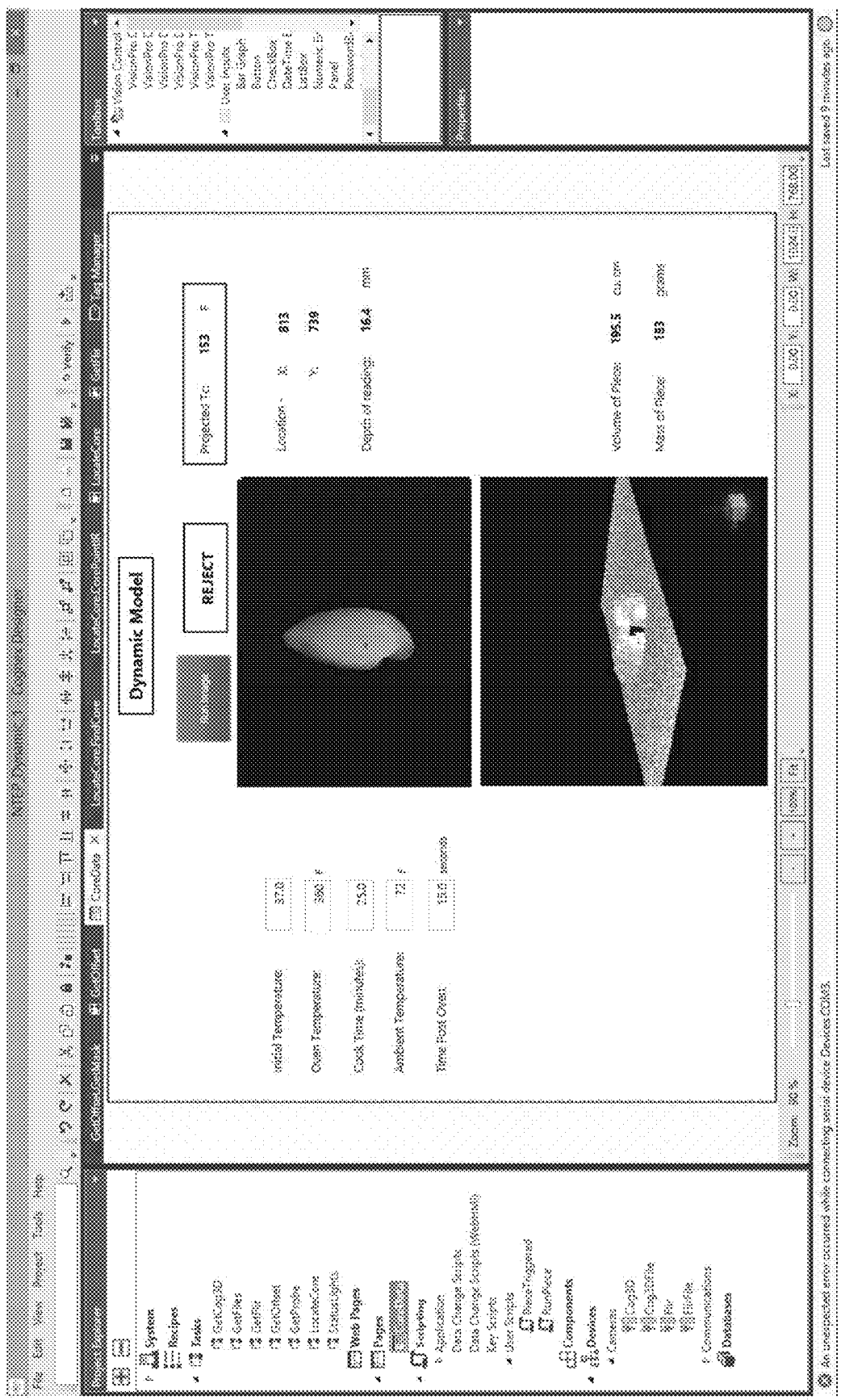
FIG. 6 is an illustration of a dynamic model illustrative of a correlated data set.
Figure 7:
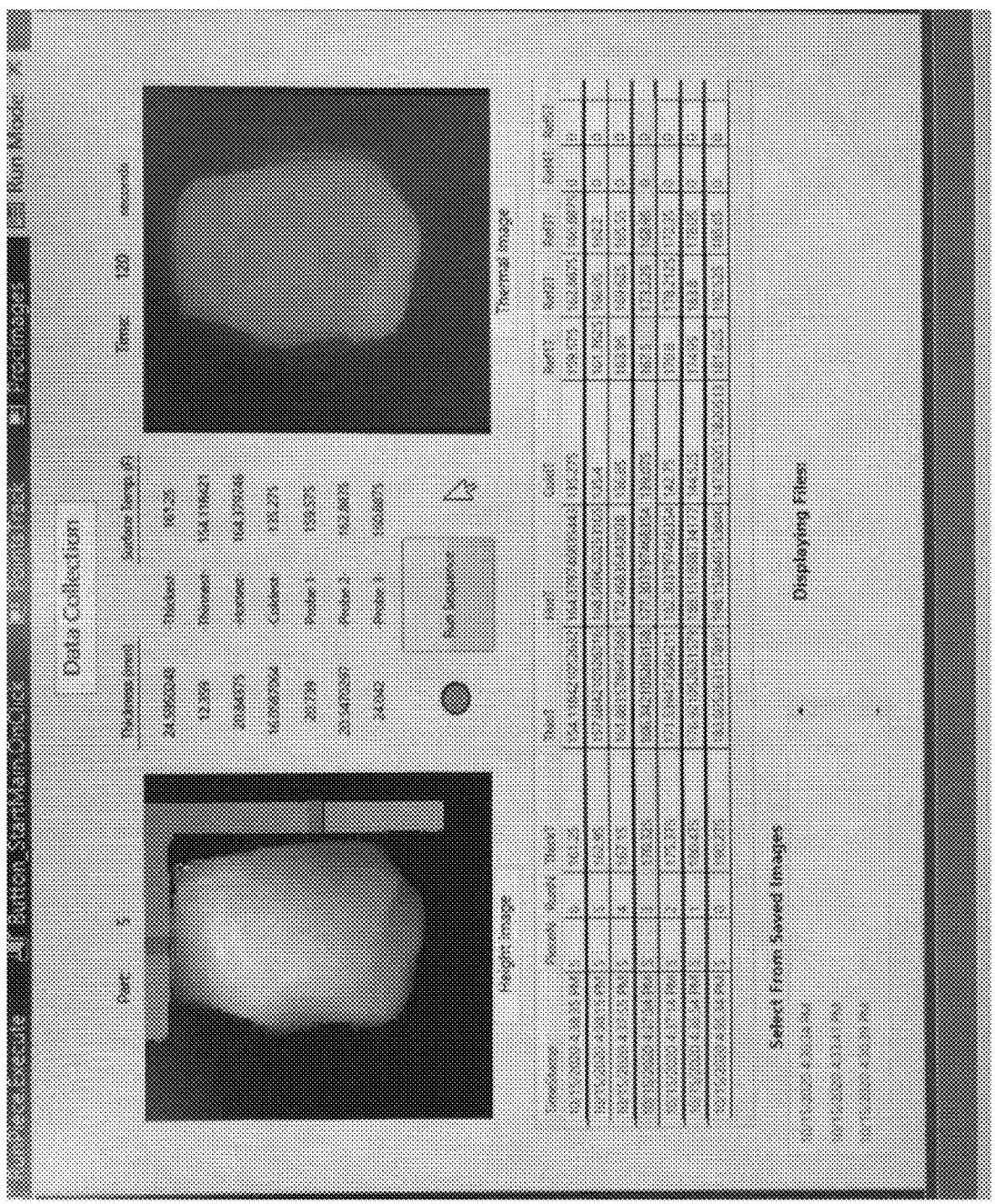
FIG. 7 is an illustration of a dynamic model illustrative of a correlated data set.
Figure 8:
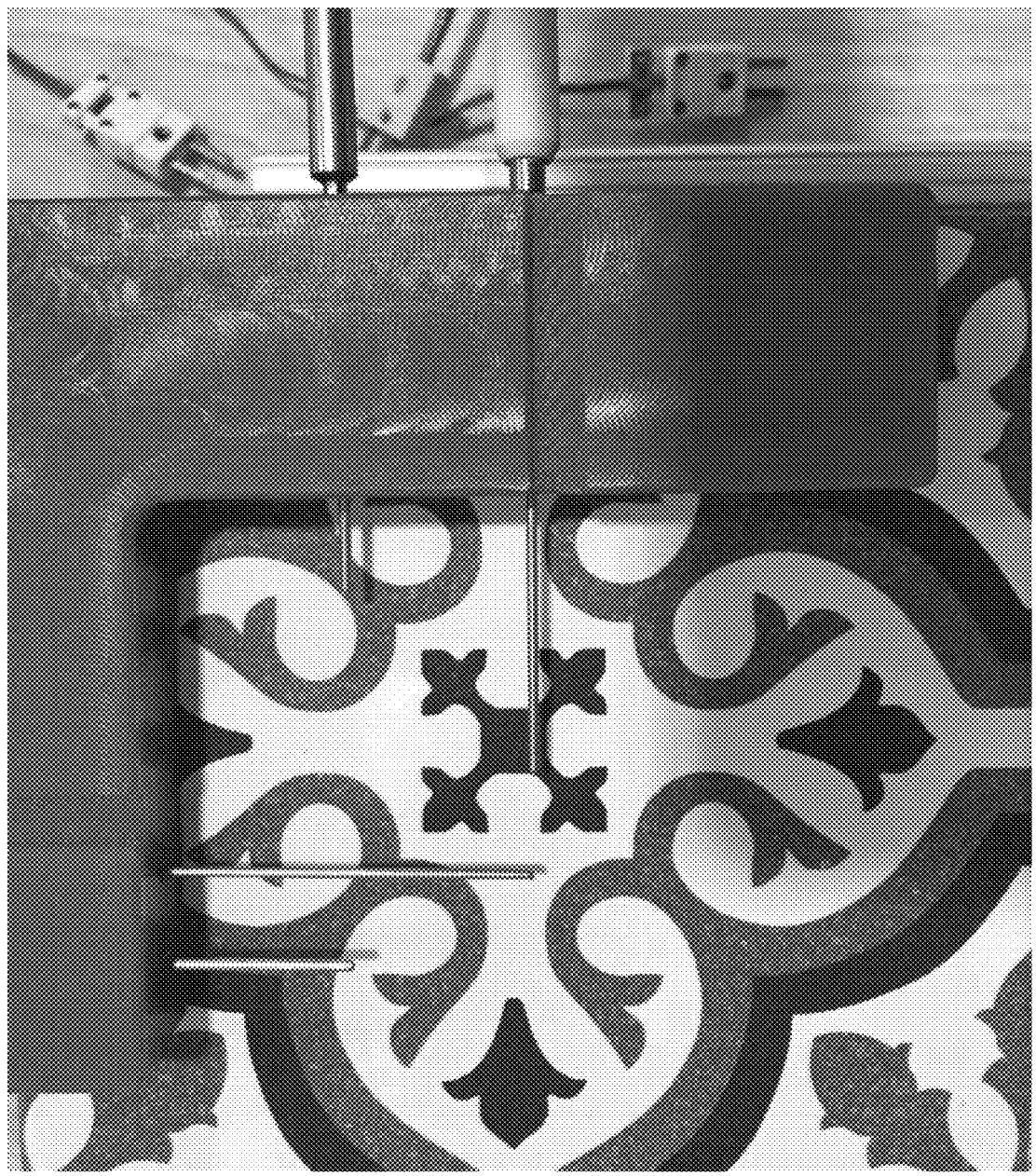
FIG. 8 is an illustration of measuring tool.

Referring to FIGS. 6, 7 and 8, an illustration of the Dynamic Model and the Data Collection is shown. Data is collected with a 3D Profile Camera for determining the geometry of an item for determination of the core position. For one implementation, a digital 3D model, such as a point cloud, is generated that is representative of the outer surface geometry that can be utilized to find the core position within the food item. An infrared camera is utilized to capture infrared data of the food item to collect heat map temperature data of the items surface. A physical direct temperature measure is taken at a calculated core position of the item as determined from the outer geometry using a temperature probe that is aligned and inserted to penetrate to the core position utilizing a robotic arm or a probe alignment fixture (SEE FIG. 8). The infrared camera acquired data is compared to and correlated with the measured data obtained by the probe. The collected and correlated data is used to determine a multifactor, multinomial relationship model and correlation with variable factors including, initial food item temperature, air temperature of the temperature processing temperature (cooking chamber temperature), thickness of meat, Cook time and Surface temperature of the food item undergoing temperature processing. The data is also correlated to constant factors including oven air temperature, absolute humidity and oven air speed.

Figure 9A:
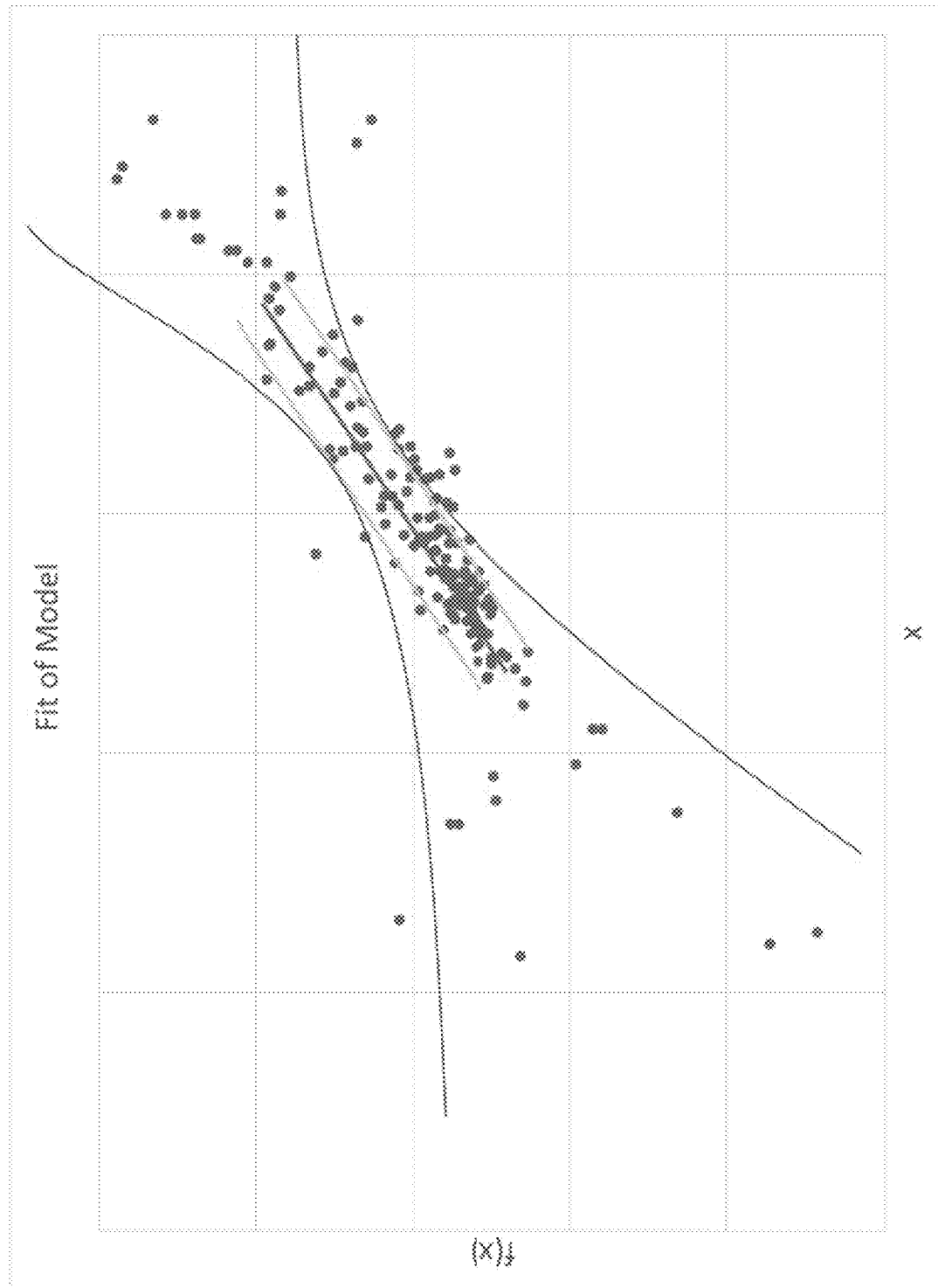
FIG. 9A is an illustration of a fit model.
Figure 9B:
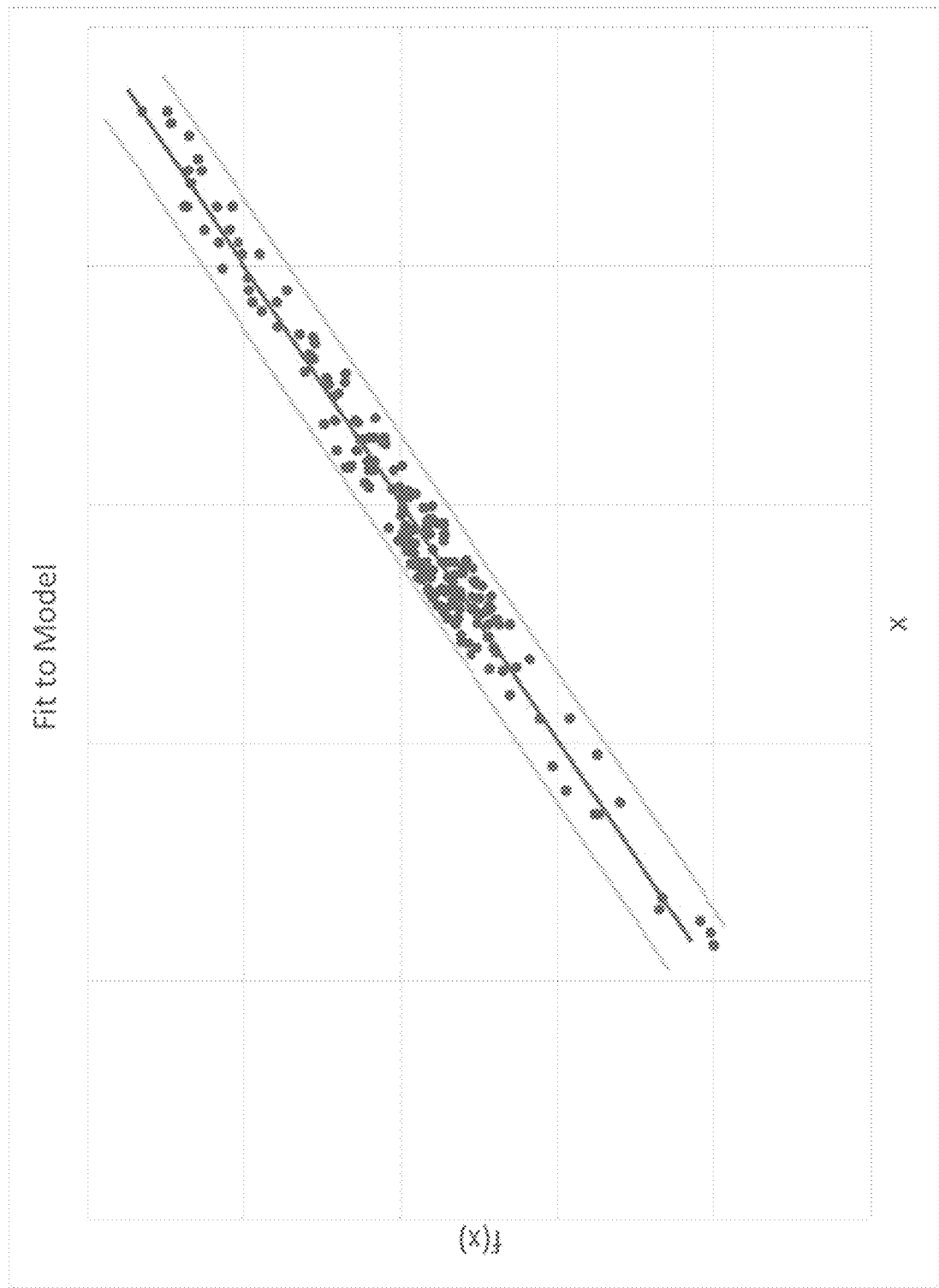
FIG. 9B is an illustration of a fit model.

Referring to FIGS. 9A and 9B, a graphical illustration of non-contact model fitting is illustrated. As data is collected corresponding to the external heat map from the infrared camera and compared to the actual physically probed core temperature, a predictive relational model is developed utilizing a regression algorithm to predict the core temperature based on the external infrared image of a given type of food item. The fit of the relational model by way of illustration is within the testing range is $R^2=0.93$. By way of illustration, depending on the heat conduction characteristics of the food item, values may diverge widely outside testing range with variation from actual values increasing with additional variation in the cook process or temperature process. By way of illustration, the chart displays the 95% confidence interval. There is severely diminished fit to model outside of the restrictions of the initial testing parameters (with $R^2$ reduced below 0.50 for the extended range). A mathematical heat conduction model is added to stabilize model variation for a limited range of process settings outside the testing range. Using infrared radiation measurement largely restricts the measurement to the outside or near surface temperature of the product. Use of shorter wavelength radiation increases the depth of reading. Since temperature measurement is restricted to upper tissue of the food item, using a mathematical heat-transfer model combined with a relational model from product testing is utilized to predict the core temperature. This has a reliability of 95% within very tight controls. A new mathematical model is developed for each variation in product type.

For one implementation of the thermal composite model a regression model is utilized where for one implementation, the primary regression model is a multivariate, multinomial equation based on comparative measures of test meat portion samples through a cook process (oven cook zone) and into the multi-camera work area (device work zone).

Some Single Factors Of Model Include:

| Single Factors | Coefficient | Description |
| --- | --- | --- |
| | z | constant |
| Height | a | Vertical thickness of selected area of the meat portion. |
| Humidity | b | Moisture content within the oven cook zone. |
| AirSpeed | c | Velocity of air movement within the oven cook zone. |
| OvenTemp | d | Temperature of the air within the oven cook zone. |
| CookTime | e | Time within the oven cook zone experienced by meat portion. |
| IRTemp | f | Emitted infrared energy expressed as temperature from selected area of the meat portion. |
| AirTemp | g | Temperature of air within the device work zone. |

Some Interaction Factors Of Model Include:

| Interaction Factors | Coefficient |
| --- | --- |
| Height*Humidity | h |
| Height*AirSpeed | i |
| Height*OvenTemp | j |
| Height*CookTime | k |
| Height*IRTemp | l |
| Height*AirTemp | (null) |
| Humidity*AirSpeed | m |
| Humidity*OvenTemp | n |
| Humidity*IRTemp | (null) |
| Humidity*AirTemp | (null) |
| AirSpeed*OvenTemp | o |
| AirSpeed*CookTime | p |
| AirSpeed*IRTemp | q |
| AirSpeed*AirTemp | (null) |
| OvenTemp*CookTime | r |
| OvenTemp*IRTemp | s |
| OvenTemp*AirTemp | (null) |
| CookTime*IRTemp | t |
| CookTime*AirTemp | u |
| IRTemp*AirTemp | v |

For one implementation of the technology as disclosed and claimed a Model Core Temperature MCT equation is illustrated by:

$$MCT = z + a*Height + b*Humidity + c*AirSpeed + d*OvenTemp + e*CookTime + f*IRTemp + g*AirTemp + a1*Height*Height + b1*Humidity*Humidity + c1*AirSpeed*AirSpeed + d1*OvenTemp*OvenTemp + e1*CookTime*CookTime + f1*IRTemp*IRTemp + g1*AirTemp*AirTemp + h*Height*Humidity + i*Height*AirSpeed + j*Height*OvenTemp + k*Height*CookTime + l*Height*IRTemp + m*Humidity*AirTemp + n*Humidity*OvenTemp + o*AirSpeed*OvenTemp + p*AirSpeed*CookTime + q*AirSpeed*IRTemp + r*OvenTemp*CookTime + s*OvenTemp*IRTemp + t*CookTime*IRTemp + u*CookTime*AirTemp + v*IRTemp*AirTemp$$

Figure 9H:
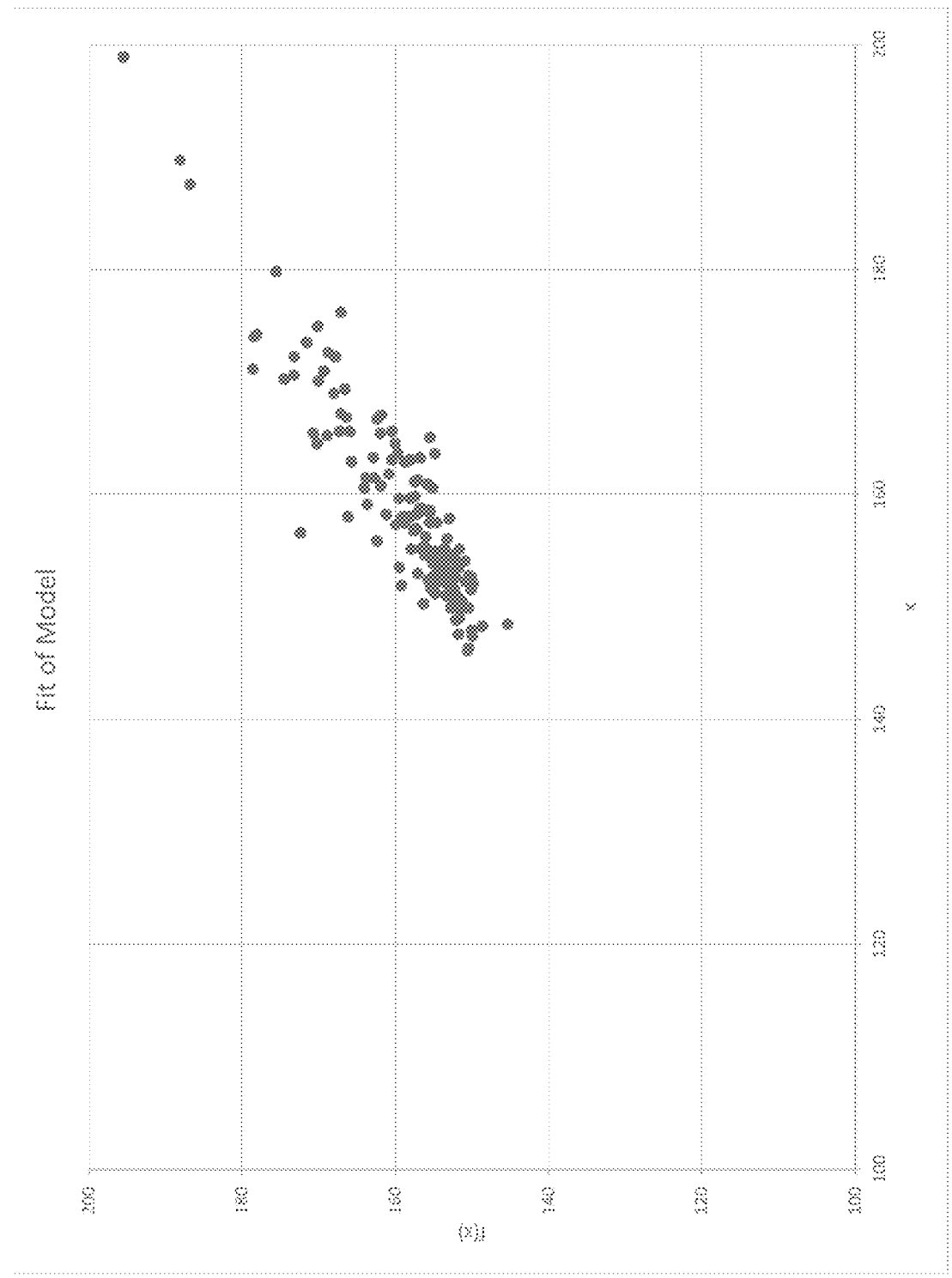

FIGS. 9C through 9G are illustrative of a core temperature model data set and FIG. 9H is a graphical illustration of a fit model based on the data set.

For one implementation of the technology as disclosed and claimed, the thermal conductivity model is a time-based simulation of heat flux movement across the thermal boundary between the oven cook zone and the meat portion and through the meat portion of a specified thickness via thermal conduction.

Factors are: 1. Heat content of oven cook zone air based dry air temperature and moisture content.
    2. Heat content of meat portion from specified starting temperature and with set heat conduction and specific heat values.
    3. Rate of moisture content loss at elevated temperature within the meat portion assuming proportional loss to energy absorption through the latent phase of vaporization Inclusive Constants and Physical Laws Include:
Specific heat of chicken 1.77 kJ/kg-K (1.77 J/g-K)
Thermal conductivity W/m-K (J/s-m-K)
W=J/s
Meat portion density is 1.12 g/cu cm
Heat of vaporization is 2260 J/g
Outside temperature is (to), expressed in ° C.
Distance to core is Height/2, expressed in meters
k is 0.475 W/m-K
A, area, is 0.02×0.02=0.0004 m^2
d, distance, is Height/2 m
difference is (t0−T0)=Tdiff
Q=0.475*0.0004/d*Tdiff
Q=0.95 J/s
material temperature change in 1 second
V=2×2×1=4 cu cm
M=4×1.12=4.48 g
dT=0.95/1.77/4.48
dT=0.1198 K
T2=Tdiff+0.1198
T2=k*A/d*(To−T0)/1.77/mass+T0
T2=(0.000009*T0^2−0.0017*T0+0.5351)*A/d*(To−T0)/1.77/mass+T0
Iteration
ThermalCoreTemperature, TCT
    TCT=Sum(Factors) for time interval (t0–tn, where tn is CookTime) through thickness (d0–dn, where do is Height/2)

For one implementation, the composite result for the core temperature value is the proportional combination of the ModelCoreTemperature, MCT, and the ThermalCoreTemperature, TCT. This gives the projected core temperature, Tc. Temperatures are expressed in ° F. with a ceiling value of 208° F. due to moisture content on meat portion.
By Way of Illustration the Pseudo Logic is as Follows:

```
Foffset = 208 − MCT;
Moffset = 208 − TCT;
Mdiff = MCT − TCT;
if( Mdiff < 0 ) {
    ProjTC = Moffset / Foffset * Mdiff + TCT;
} else {
    ProjTC = Foffset / Moffset * Mdiff + TCT;
}
Tc = ProjTC;
```

One implementation of the technology as disclosed and claimed utilizes cooking historical temperature profile data for a food item correlated with corresponding historical 3D geometric profile data of the food item captured with a 3D profile camera to determine the core position, with the corresponding infrared radiation heat map of the outer temperature profile of the food item captured by the infrared camera, and with historical corresponding historical temperature probe measurements at the determined core position to thereby generate a predictive model for the core temperature of a cooked food item, whereby the physical temperature probe can be either totally eliminated or performed periodically for a calibration check and calibration adjustment and for continuous improvement of the thermal model by way of a learning function.

Figure 10B:
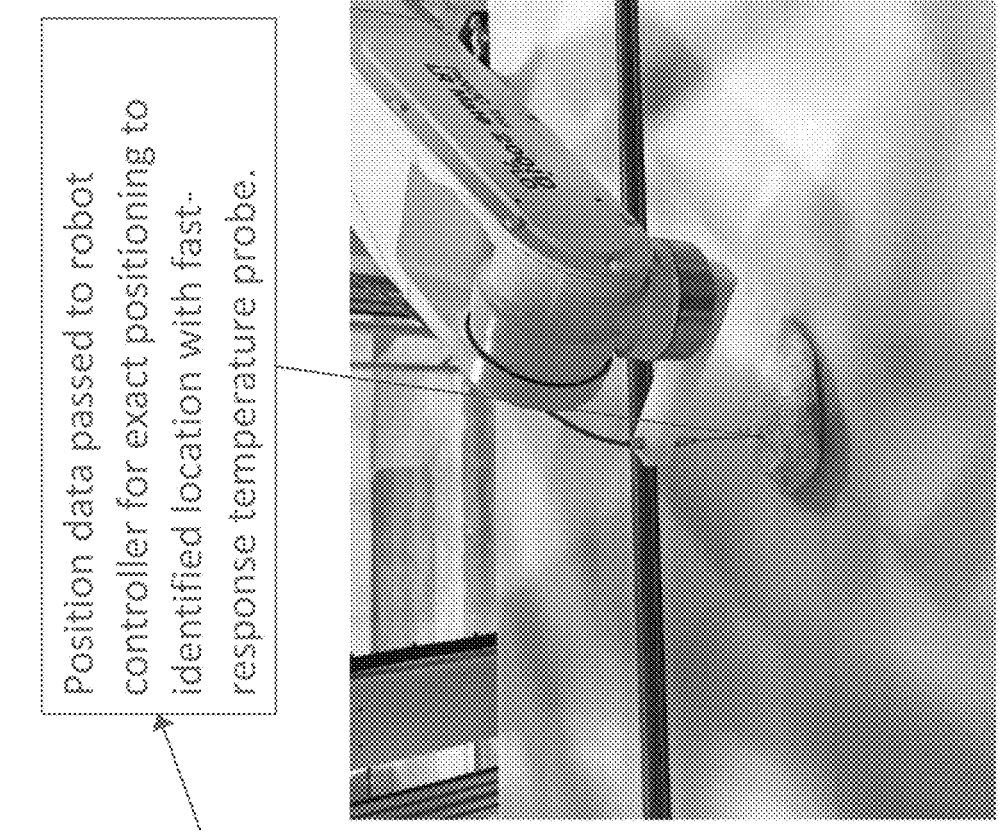
FIGS. 10A and 10B is an illustration of the position data being passed to the controller for location of the temperature probe.
Figure 10A:
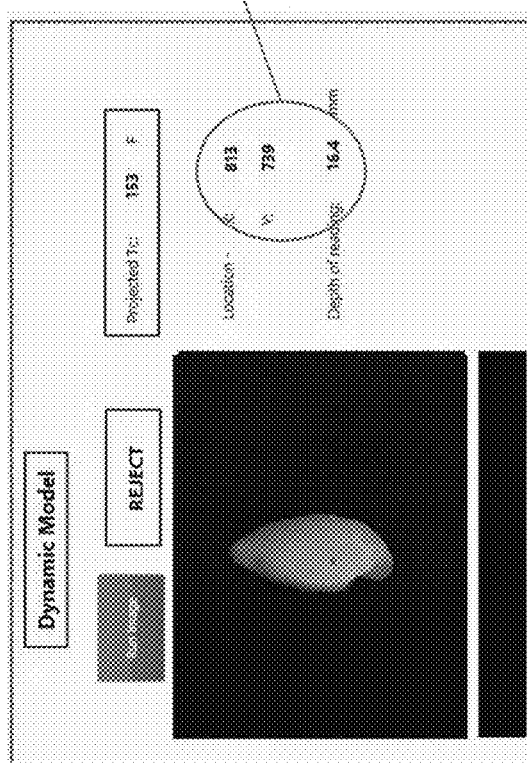
Figure 10C:
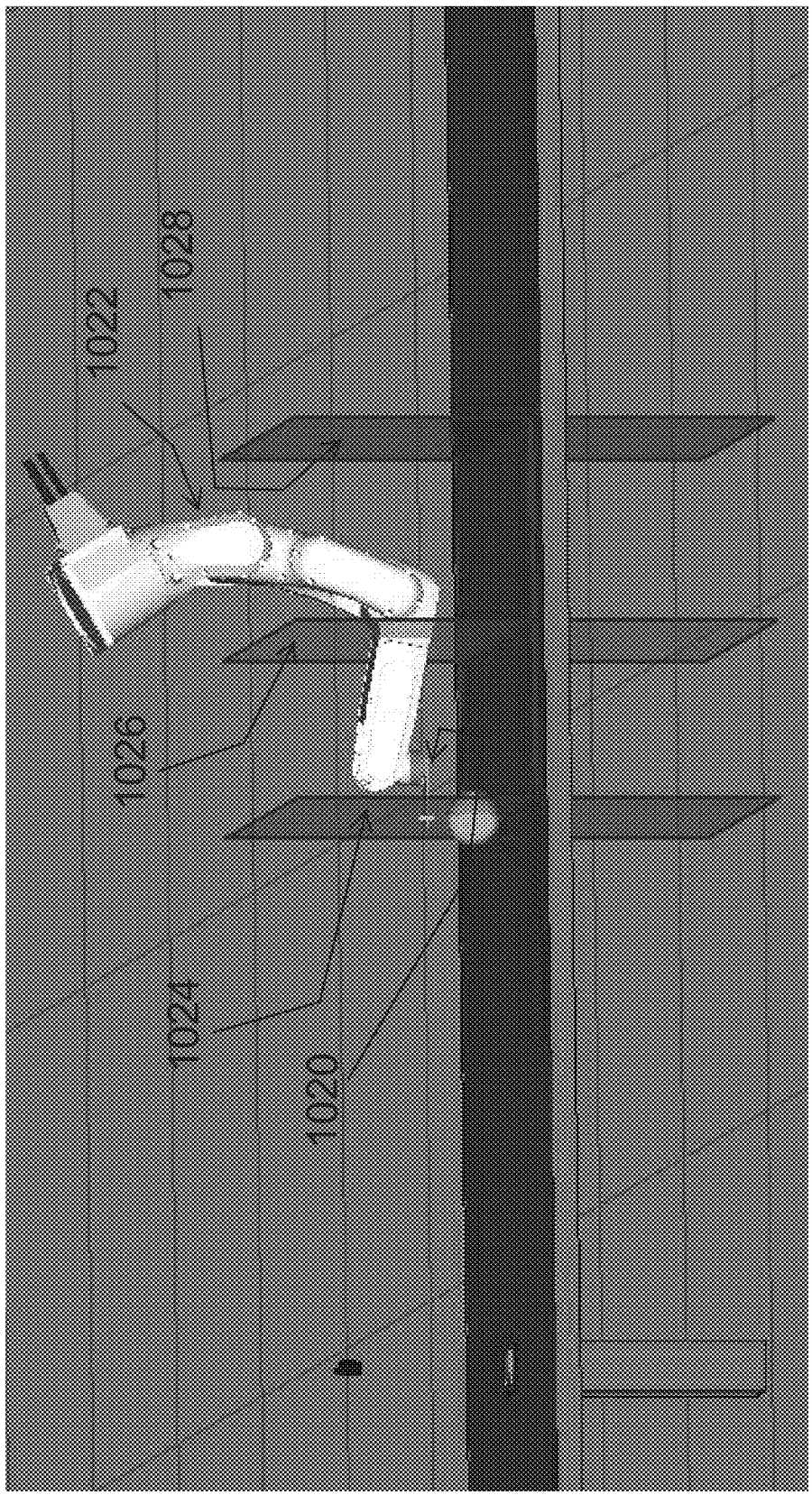
FIG. 10C is a further illustration of the robotic arm operation.

Referring to FIGS. 10A and 10C, one implementation of the technology as disclosed and claimed herein utilizes 3D geometric profile data of the food item captured with a 3D profile camera to determine the core position of a food item based on a determined geometric profile of a food item derived from 3D geometric profile data of the food item to thereby control a 6-axis, 7-axis or greater robotic arm 1022 configured to hold and position a temperature probe at the core position to thereby measure the temperature at the core position; and the technology for one implementation further correlates the geometric profile with the measured temperature to build a historical reference database that correlates the geometry of an item with a core temperature that is operated on by a learning function to thereby build a predictive model to thereby determine which of the individual food items being processed along the production run is most likely to have the coldest possible core temperatures in the product stream. The learning function further refines image processing from 3D camera to more accurately determine the core position and to measure the core position temperature of the food items. The temperature process profile that a food item undergoes, by way of illustration, the temperature process profile of a linear oven, is correlated to an item geometry and a core temperature for core temperature prediction for a food item.

Figure 10D:
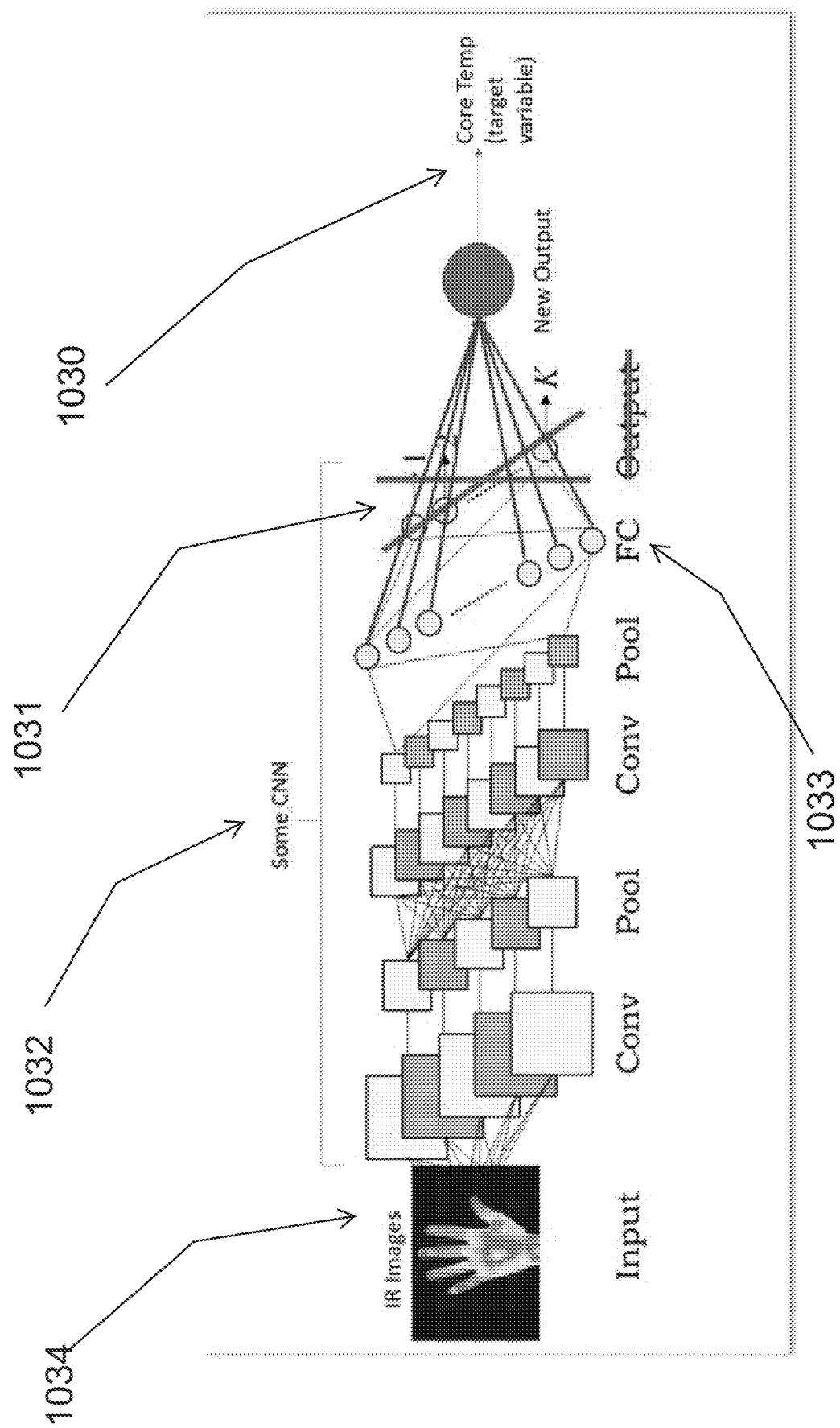
FIG. 10D is an illustration of a machine learning model.
Figure 10F:
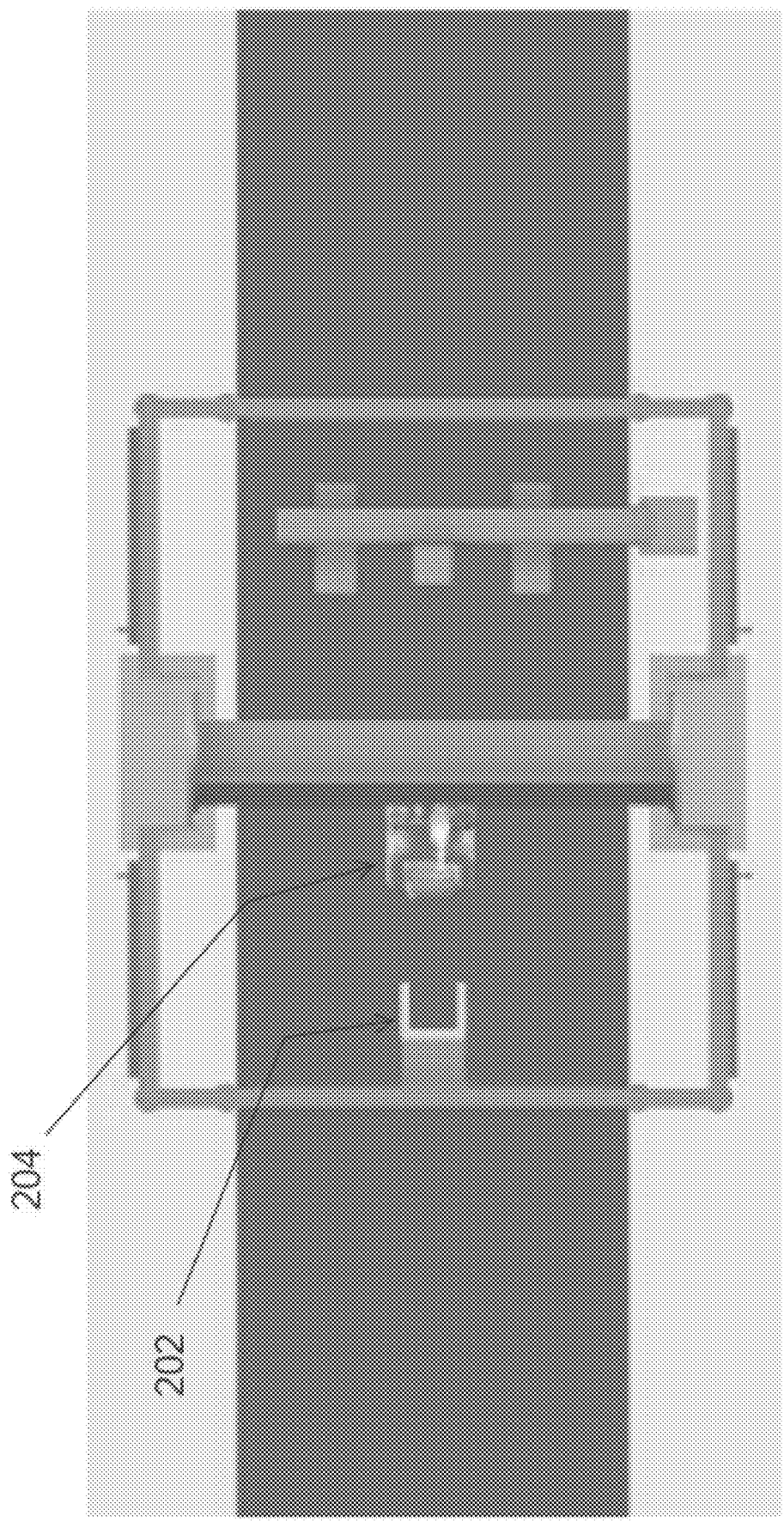

Referring to FIG. 10D, with regard to the machine learning approach for core temperature prediction, one implementation comprises two steps including a model selection process that will select from among a plurality of separately trained product models whereby the selection is made base on one or more of a manual input indicative of the product being process and an automated classification model that identifies the product being processed utilizing an RGB camera/sensor, an IR sensor, and a 3D camera/sensor to disambiguate between the various types of products that could be processed. One implementation of the machine learning includes a convolutional neural network 1032 (CNN, likely ResNet or Inception; machine learning architecture typically used for images classification problems), but whose architecture will replace the output layer 1031 with a single node that uses a linear activation function 1033 for regression to predict core temperature as a continuous output variable 1030 instead of a discrete class.

For one implementation of the predictive model and machine learning, the technology as disclosed and claimed herein includes the use of a 16-bit IR image 1034 and (x,y) coordinates of the probe insertion, cropping a relative part of the image centered around the probe insertion, and downsampling accordingly. For one implementation of the predictive model and machine learning the technology utilizes 3D image data as an additional channel for the input layer. For one implementation of the predictive model and machine learning the technology utilizes a more complex model architecture that integrates any of volume, mass, oven temp, cook time, etc as input parameters. While this will demand an exponentially larger data set for training, it is also likely that a dilutional algorithm is leveraged or similar to select for weight estimation from stronger predictive features to reduce this constraint.

For one implementation, as illustrated in FIG. 10C, the robotic arm 1022 can probe a new food item every approximately 3-4 seconds. Coordinate Position Data is transmitted to the robot controller for positioning a fast response temperature probe 1020 to the identified location. Referring to FIG. 10C, a further illustration of the robotic arm 1022 is provided. The First Plane 1024 is the Upper limit of the robot's operation This is will be the start of the robot reach during tracking as product is being conveyed along a path of conveyance. The Second Plane 1026 is the "Pick By" plane. This is the point that the robot will have the temperature reading started by. The Third Plane 1028 is the Lower limit of the robot. The robot will not be able to take a temperature passed this point. It is important to maintain these ranges in order to assure the consistence of the measurements being conveyed a specific distance from the temperature treatment process. FIGS. 10D and 10E is an illustration of the non-contact measurement system including the robotic arm and temperature probe assembly 204 and a 3D Camera. FIGS. 10F through 10I illustrates one implementation of the non-contact measurement system including a calculation and calibration tool for the robotic arm 1060, an IR sensor 1052 and a 3D camera 1050. The system also includes a conveyor system 1054 for conveying the items by the non-contact temperature measurement system where the conveyance system includes a position encoder.

For one implementation of the technology as disclosed and claimed herein, the robotic arm function includes some basic logic of primary control routines for robotic temperature measurement. One basic function includes probe calibration comprising, a Start routine, Prompt entry of temperature value into the Ignition, Trigger the robot move into heat position (center of water bath opening, probe tip 1⅞" below lid), probe Settles 2 seconds, robotic arm sends complete indication to PLC, the robotic arm moves back to a rest or stowed position. The reading is compared to a value, and updating the offset value, and the routine is complete.

The Following is the Run Operation:

Start routine.

Robot moves to perch position.

Trigger Cognex and Flir image acquisition. Store acquire date-time.

Cognex acquires image and process image. If objects, send complete and coordinates. If no objects, no communication.

Trigger robot move to coordinates plus time on Y. Track for 1.7 seconds. Send complete to PLC. Move to perch position.

Ignition update and response to reading.

If reading <Tc, trigger belt rejection and alarm.

If time from robot move >15 seconds, move robot into heat position. If complete from Cognex, move to perch position (ignore the coordinates).

Cycle routine until Operation Stop.

The following is an illustration of Robot/Cognex Calibration:

Start routine.

Place frustrum on belt.

Cognex sends complete and coordinates to PLC.

PLC stops belt with encoder position.

Prompt user to move robot to frustrum position.

User to Ignition complete.

PLC sets coordinate transform and timing offset.

Routine complete.

Glossary

Heat position: Based off location of water bath. Probe tip is center of opening of water bath and 1⅞" below the lid. Need at least 1 inch of probe in water for calibration. Fill water level is ½" below lid. This allows for ⅜" of evaporation loss.

Perch position: Location of probe between product readings. Location is center of belt at start of tracking range, positioned 4" above belt surface.

Rest position: Location of probe outside operation.

Drop position: Location above previous insertion exit. At height of 4" above belt surface.

Figure 11A:
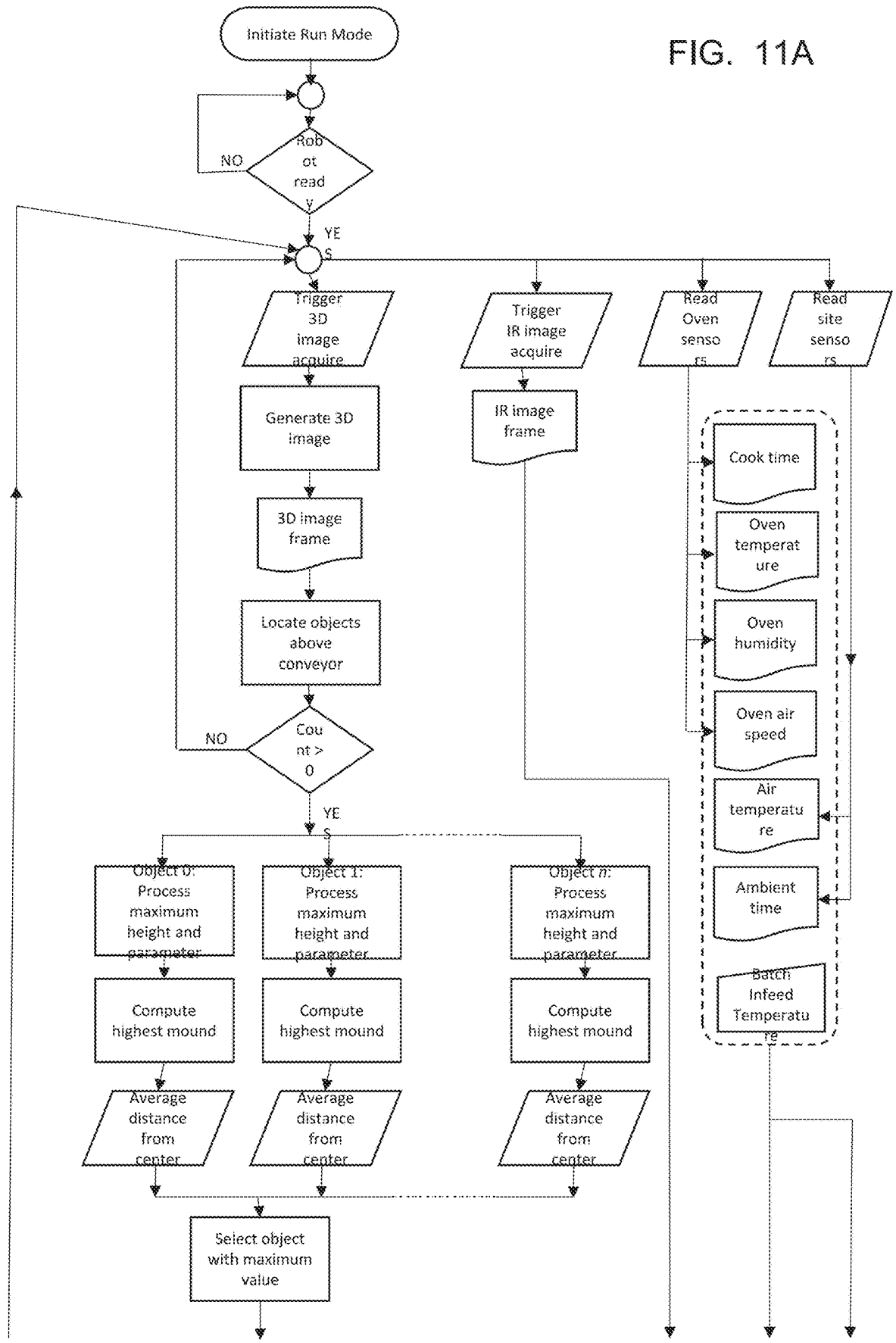
FIGS. 11A and 11B are an illustration of the non-contact temperature probe process flow.
Figure 11B:
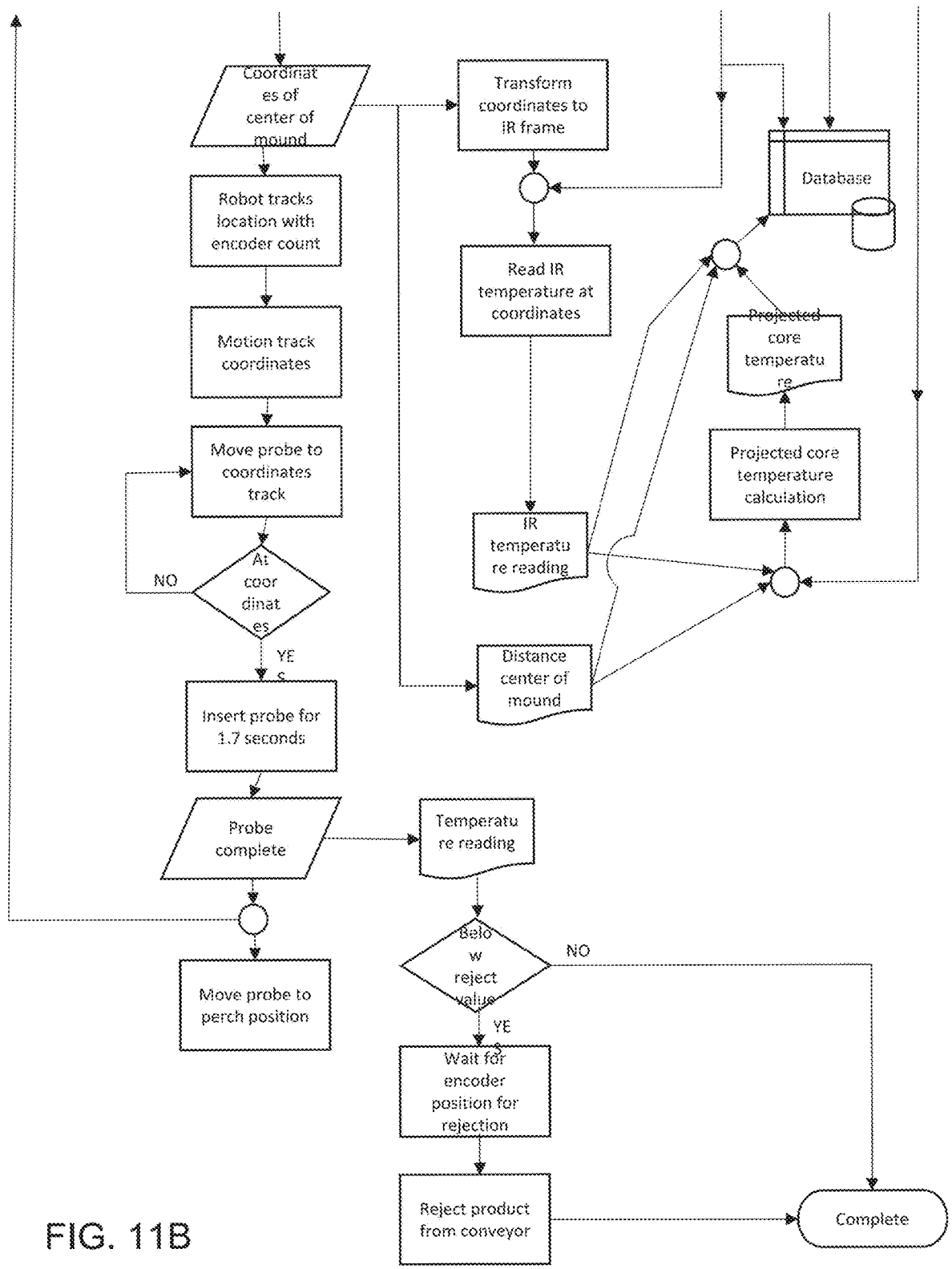

Referring to FIGS. 11A and 11B, an illustration of the non-contact temperature probe process flow is provided. The process run mode is initiated and the robotic arm status is checked for ready position and then the ready position is confirmed YES, the 3D camera is triggered to acquire a 3D image of items being conveyed and the near IR scanner is triggered to acquire and IR image and the oven sensors are read and the site sensors are read. The 3D image is evaluated to locate product on the conveyor. If no product is detected, the 3D camera is repetitively triggered to acquire the 3D image. An IR image frame is captured. The maximum distance from the outer edges is determined. The 3D Camera image of an object is processed by a computing system determining maximum height, computing highest mound and average distance from center. An object having the maximum value is selected and coordinated of a center mound is determined. The coordinates of an object is tracked using an encoder. For one implementation the robotic are is tracks to the coordinates and inserts the probe. The coordinates of the center mound is transformed to coordinates in an IR Frame and the IR temperature is read at the coordinates. The projected core temperature is calculated.

Referring to FIGS. 12A through 12E, an illustration of the selection of a temperature probing point within a multiple piece food item flow. Upon activation, an image is triggered from the 3D displacement camera. The image has been adjusted for the belt surface height and calibrated with the robot coordinates system. A 3D surface image is produced. This is an overhead vision camera shot of the same area of belt to convey how the image is processed. All structures that are above the conveyor by a certain minimum height and conform to a minimum size are identified as objects. In this case, there are 9 objects within the 3D camera frame. Each object is further processed according to the maximum height of the object and its parameter to identify the mound. The mound is considered a contiguous high area not adjoining the outer parameter by half of the maximum height value. The average height of the center of this mound is identified for the object. The object with the highest value is selected. From the selected object, the center of the mound area is identified as the core location to be used as coordinates for the temperature probe measurement. In this case, the $3^{rd}$ piece from the left of the back row is selected by the criterion. The point for the temperature probe to be positioned at is highlighted. The 3-dimensional coordinates for this point is passed to the robot controller after processing of the image.

One implementation of the technology as disclosed and claimed is an apparatus for thermal processing of a food item including a historical reference database 212 including a plurality of sample heat maps for one or more different sample food items 106 each having an associated sample outer geometry correlated to a sample physically measured core temperature in a core area for each of the one or more different sample food items, where each of the heat maps and correlated measured core temperatures are associated with a time/temperature profile for the one or more different food items. The technology includes a controller computing system 210 analyzing the historical reference database by processing a learning algorithm to thereby adjust the time/temperature profiles, see illustration in FIGS. 4 and 5, and a position of the core area and provide a predictive multifactor, multinomial relational model utilizing a regression algorithm to thereby predict an actual core temperature based on an actual heat map. For one implementation a conveyor is communicably linked to controlled by a controller computing system to convey one or more actual food items through a temperature processing chamber and controlling the temperature processing chamber to perform a time/temperature profile as the one or more actual food items are conveyed 214 through the temperature processing chamber 216. For one implementation, an IR scanner 220 and a 3D camera 218 disposed at an exit end of the temperature processing chamber, where said IR scanner and 3D camera a communicably linked to and thereby controlled by the controller computing system 210 to control the IR Scanner to capture an IR image and translate to the actual heat map for each of the one or more actual food items and to control the 3D camera to capture a 3D image and translate to an actual surface geometry for each of the one or more actual food items. For on implementation the controller computing system has a predictive multifactor, multinomial relational model processing to thereby analyze the actual heat map for each of the one or more actual food items thereby predicting the actual core temperature for the one or more food items based on the actual heat map of the one or more food items. For one implementation he positon of the core area within the food item is the farthest from all surfaces of the associated outer geometry. For one implementation the predictive multifactor, multinomial relational model is correlated with variable factors including, an initial food temperature, an air temperature, a processing temperature of the temperature processing chamber, thickness of food item, and where the predictive multifactor multinomial relational model is correlated to constant factors including oven air temperature, absolute humidity and oven air speed. For one implementation the predictive multifactor, multinomial relational model includes a thermal conductivity model. For one implementation predicting the actual core temperature uses the machine learning algorithm to provide the predictive multifactor, multinomial relational model, where said machine learning algorithm includes a convolutional neural network. For one implementation predicting the actual core temperature using the machine learning algorithm to provide the predictive multifactor, multinomial relational model utilizes one or more of food item volume, food item mass, thermal processing temperature, and thermal processing time as input parameters. For one implementation a historical reference database including a plurality of sample heat maps for one or more different sample food items each has an associated sample outer geometry correlated to a sample physically measured core temperature in a core area for each of the one or more different sample food items, where each of the heat maps and correlated measured core temperatures are associated with a time/temperature profile for the one or more different food items, where the sample physically measured core temperature is measured using a temperature probe inserted by a robotic arm 222.

The various implementations and examples shown above illustrate a method and system for non-contact temperature measurement. A user of the present method and system may choose any of the above implementations, or an equivalent thereof, depending upon the desired application. In this regard, it is recognized that various forms of the subject non-contact method and system could be utilized without departing from the scope of the present technology and various implementations as disclosed.

As is evident from the foregoing description, certain aspects of the present implementation are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the and scope of the present implementation(s). Accordingly, the specification and drawings are to be regarded in an illustrative rather than a restrictive sense.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled. The inventive subject matter may be represented in a variety of different implementations of which there are many possible permutations.

The methods described herein do not have to be executed in the order described, or in any particular order. Moreover, various activities described with respect to the methods identified herein can be executed in serial or parallel fashion. In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

In an example implementation, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine or computing device. Further, while only a single machine is illustrated, the term "machine" shall also be taken to include any collection of machines that individually or jointly execute a set (or multiple sets) of instructions to perform any one or more of the methodologies discussed herein.

The example computer system and client computers can include a processor (e.g., a central processing unit (CPU) a graphics processing unit (GPU) or both), a main memory and a static memory, which communicate with each other via a bus. The computer system may further include a video/graphical display unit (e.g., a liquid crystal display (LCD) or a cathode ray tube (CRT)). The computer system and client computing devices can also include an alphanumeric input device (e.g., a keyboard), a cursor control device (e.g., a mouse), a drive unit, a signal generation device (e.g., a speaker) and a network interface device.

The drive unit includes a computer-readable medium on which is stored one or more sets of instructions (e.g., software) embodying any one or more of the methodologies or systems described herein. The software may also reside, completely or at least partially, within the main memory and/or within the processor during execution thereof by the computer system, the main memory and the processor also constituting computer-readable media. The software may further be transmitted or received over a network via the network interface device.

The term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present implementation. The term "computer-readable medium" shall accordingly be taken to include, but not be limited to, solid-state memories, and optical media, and magnetic media.

The various temperature measurement implementations shown above illustrate a non-contact method and apparatus. A user of the present technology as disclosed may choose any of the above implementations, or an equivalent thereof, depending upon the desired application. In this regard, it is recognized that various forms of the subject non-contact temperature measurement apparatus and method could be utilized without departing from the scope of the present invention.

As is evident from the foregoing description, certain aspects of the present technology as disclosed are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the scope of the present technology as disclosed and claimed.

Other aspects, objects and advantages of the present technology as disclosed can be obtained from a study of the drawings, the disclosure and the appended claims.

What is claimed is:

1. An apparatus for thermal processing of a food item comprising:
   a historical reference database including a plurality of sample heat maps for one or more different
      sample food items each having an associated sample outer geometry correlated to a sample physically measured core temperature in a core area for each of the one or more different sample food items, where each of the heat maps and correlated measured core temperatures are associated with a time/temperature profile for the one or more different food items;
   a controller computing system analyzing the historical reference database by processing a learning algorithm to thereby adjust the time/temperature profiles and a position of the core area and provide a predictive multifactor, multinomial relational model utilizing a regression algorithm to thereby predict an actual core temperature based on an actual heat map;
   a conveyor communicably linked to controlled by a controller computing system to convey one or more actual food items through a temperature processing chamber and controlling the temperature processing chamber to perform a time/temperature profile as the one or more actual food items are conveyed through the temperature processing chamber;
   an IR scanner and a 3D camera disposed at an exit end of the temperature processing chamber, where said IR scanner and 3D camera a communicably linked to and thereby controlled by the controller computing system to control the IR Scanner to capture an IR image and translate to the actual heat map for each of the one or more actual food items and to control the 3D camera to capture a 3D image and translate to an actual surface geometry for each of the one or more actual food items; and
   said controller computing system having the predictive multifactor, multinomial relational model processing to thereby analyze the actual heat map for each of the one or more actual food items thereby predicting the actual core temperature for the one or more food items based on the actual heat map of the one or more food items.

2. The apparatus for thermal processing as recited in claim 1, where the positon of the core area within the food item is the farthest from all surfaces of the associated outer geometry.

3. The apparatus for thermal processing as recited in claim 1, where the predictive multifactor, multinomial relational model is correlated with variable factors including, an initial food temperature, an air temperature, a processing temperature of the temperature processing chamber, thickness of food item, and where the predictive multifactor multinomial relational model is correlated to constant factors including oven air temperature, absolute humidity and oven air speed.

4. The apparatus for thermal processing as recited in claim 3, where the predictive multifactor, multinomial relational model includes a thermal conductivity model.

5. The apparatus for thermal processing as recited in claim 1, where predicting the actual core temperature using the machine learning algorithm to provide the predictive multifactor, multinomial relational model, where said machine learning algorithm includes a convolutional neural network.

6. The apparatus for thermal processing as recited in claim 1, where predicting the actual core temperature using the machine learning algorithm to provide the predictive multifactor, multinomial relational model utilizes one or more of food item volume, food item mass, thermal processing temperature, and thermal processing time as input parameters.

7. A method for thermal processing of a food item comprising:
   storing in a historical reference database a plurality of sample heat maps for one or more different
      sample food items each having an associated sample outer geometry correlated to a sample physically measured core temperature in a core area for each of the one or more different sample food items, where each of the heat maps and correlated measured core temperatures are associated with a time/temperature profile for the one or more different food items;
   analyzing with a controller computing system the historical reference database by processing a learning algorithm to thereby adjust the time/temperature profiles and a position of the core area and provide a predictive multifactor, multinomial relational model utilizing a regression algorithm to thereby predict an actual core temperature based on an actual heat map;

communicably linking a conveyor to a controller computing system to control and convey one or more actual food items through a temperature processing chamber and controlling the temperature processing chamber to perform a time/temperature profile as the one or more actual food items are conveyed through the temperature processing chamber;

communicably linking an IR scanner and a 3D camera disposed at an exit end of the temperature processing chamber, to and thereby controlling with the controller computing system to control the IR Scanner to capture an IR image and translate to the actual heat map for each of the one or more actual food items and to control the 3D camera to capture a 3D image and translate to an actual surface geometry for each of the one or more actual food items; and processing the predictive multifactor, multinomial relational model on said controller computing system to thereby analyze the actual heat map for each of the one or more actual food items thereby predicting the actual core temperature for the one or more food items based on the actual heat map of the one or more food items.

8. The method for thermal processing as recited in claim 7, where the positon of the core area within the food item is the farthest from all surfaces of the associated outer geometry.

9. The method for thermal processing as recited in claim 7, where the predictive multifactor, multinomial relational model is correlated with variable factors including, an initial food temperature, an air temperature, a processing temperature of the temperature processing chamber, thickness of food item, and where the predictive multifactor multinomial relational model is correlated to constant factors including oven air temperature, absolute humidity and oven air speed.

10. The method for thermal processing as recited in claim 9, where the predictive multifactor, multinomial relational model includes a thermal conductivity model.

11. The method for thermal processing as recited in claim 7, where predicting the actual core temperature using the machine learning algorithm to provide the predictive multifactor, multinomial relational model, where said machine learning algorithm includes a convolutional neural network.

12. The apparatus for thermal processing as recited in claim 7, where predicting the actual core temperature using the machine learning algorithm to provide the predictive multifactor, multinomial relational model utilizes one or more of food item volume, food item mass, thermal processing temperature, and thermal processing time as input parameters.

13. An apparatus for thermal processing of a food item comprising:

a historical reference database including a plurality of sample heat maps for one or more different sample food items each having an associated sample outer geometry correlated to a sample physically measured core temperature in a core area for each of the one or more different sample food items, where each of the heat maps and correlated measured core temperatures are associated with a time/temperature profile for the one or more different food items, where the sample physically measured core temperature is measured using a temperature probe inserted by a robotic arm;

a controller computing system analyzing the historical reference database by processing a learning algorithm to thereby adjust the time/temperature profiles and a position of the core area and provide a predictive multifactor, multinomial relational model utilizing a regression algorithm to thereby predict an actual core temperature based on an actual heat map;

a conveyor communicably linked to controlled by a controller computing system to convey one or more actual food items through a temperature processing chamber and controlling the temperature processing chamber to perform a time/temperature profile as the one or more actual food items are conveyed through the temperature processing chamber;

an IR scanner and a 3D camera disposed at an exit end of the temperature processing chamber, where said IR scanner and 3D camera a communicably linked to and thereby controlled by the controller computing system to control the IR Scanner to capture an IR image and translate to the actual heat map for each of the one or more actual food items and to control the 3D camera to capture a 3D image and translate to an actual surface geometry for each of the one or more actual food items; and said controller computing system having the predictive multifactor, multinomial relational model processing to thereby analyze the actual heat map for each of the one or more actual food items thereby predicting the actual core temperature for the one or more food items based on the actual heat map of the one or more food items.

14. The apparatus for thermal processing as recited in claim 13, where the positon of the core area within the food item is the farthest from all surfaces of the associated outer geometry.

15. The apparatus for thermal processing as recited in claim 14, where the robotic arm is a 6 axis robotic arm.

16. The apparatus for thermal processing as recited in claim 13, where the position of the core area is the center of a mound area, which is a contiguous high area not adjoining an outer parameter by half of the maximum height value.

* * * * *